(12) United States Patent
Kurihara et al.

(10) Patent No.: US 10,537,623 B2
(45) Date of Patent: Jan. 21, 2020

(54) IMMUNITY INDUCTION AGENT

(71) Applicant: TORAY INDUSTRIES, INC., Tokyo (JP)

(72) Inventors: Akira Kurihara, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 37 days.

(21) Appl. No.: 14/869,523

(22) Filed: Sep. 29, 2015

(65) Prior Publication Data

US 2016/0106823 A1    Apr. 21, 2016

Related U.S. Application Data

(62) Division of application No. 14/118,417, filed as application No. PCT/JP2012/062749 on May 18, 2012, now abandoned.

(30) Foreign Application Priority Data

May 19, 2011  (JP) ................................. 2011-112210

(51) Int. Cl.
| | |
|---|---|
| *A61K 39/00* | (2006.01) |
| *A61K 39/39* | (2006.01) |
| *A61K 38/21* | (2006.01) |
| *A61K 38/44* | (2006.01) |
| *A61K 38/20* | (2006.01) |
| *C12N 9/02* | (2006.01) |

(52) U.S. Cl.
CPC .......... *A61K 39/0011* (2013.01); *A61K 38/20* (2013.01); *A61K 38/21* (2013.01); *A61K 38/44* (2013.01); *A61K 39/39* (2013.01); *C12N 9/0071* (2013.01)

(58) Field of Classification Search
None
See application file for complete search history.

(56) References Cited

U.S. PATENT DOCUMENTS

| | | | |
|---|---|---|---|
| 5,595,756 A * | 1/1997 | Bally .................... | A61K 9/1272 264/4.1 |
| 5,698,296 A | 12/1997 | Pfreundschuh | |
| 5,976,539 A * | 11/1999 | Scott .................... | A61K 38/208 424/184.1 |

FOREIGN PATENT DOCUMENTS

| | | |
|---|---|---|
| CA | 2773083 A1 | 3/2011 |
| EP | 1496109 A1 | 1/2005 |
| EP | 2030984 A1 | 3/2009 |
| WO | WO 00/09754 A2 | 2/2000 |
| WO | WO 02/074786 A2 | 9/2002 |
| WO | WO 03/016475 A2 | 2/2003 |
| WO | WO 2006/109943 A1 | 10/2006 |

OTHER PUBLICATIONS

Bowie et al. Deciphering the message in protein sequences: tolerance to amino acid substitution. Science, 247:1306-1310, 1990.*
Whisstock et al. Predication of protein function from protein sequence and structure. Quarterly Reviews in Biophysics. 36(3):307-340, 2007.*
Lazar et al. Transforming growth factor alpha: mutation of aspartic acid 47 nad leucine 48 results in different biological activities. Molecular Cellular Biology. 1988; 8(3):1247-1252.*
Zhang et al., "201 The Scd Gene Functions as a Tumor Suppressor in Leukemia Stem Cells," 52th Annual Meeting of the American-Society-of-Hematology (ASH), Blood, vol. 116, No. 21, Dec. 6, 2010.*
Scaglia et al. Inhibition of Stearoyl-CoA Desturase 1 expression in human lung adenocarcinoma cells impairs tumorigenesis. International Journal of Oncology, 2008; 33:839-850.*
Minville-Walz et al. Inhibition of Stearoyl-CoA Desaturase 1 Expression Induces Chop-Dependent Cell Death in Human Cancer Cells. Plos One, 2010; 5(12):e14363.*
Heppner et al. Tumor heterogeneity biological implications and therapeutic consequences.Cancer Metastasis Review 2:5-23; 1983.*
Jain RK. Barreirs to drug delivery in solid tumors. Scientific American, Jul. 1994, 58-65.*
Zhang, H., & Li, S. 2010). Blood, 116(21), 201. (Year: 2010).*
Minville-Walz et al. PLOS One, 2010; 5(12):e14363 (Year: 2010).*
Scaglia et al. International Journal of Oncology, 2008; 33(4):839-950 (Year: 2008).*
Buonaguro et al. Clinical and Vaccine Immunology, 2011; 18(1):23-34 (Year: 2011).*
Heppner et al. (Cancer Metastasis Review 2:5-23; 1983 (Year: 1983).*
Jain RK. Scientific American, Jul. 1994, 58-65 (Year: 1994).*
Zhang et al. The Scd1 Gene Functions as a Tumor Suppressor in Leukemia Stem Cells. Blood, 2010; 116(21), 201 (Year: 2010).*

(Continued)

*Primary Examiner* — Vanessa L. Ford
*Assistant Examiner* — Sandra E Dillahunt
(74) *Attorney, Agent, or Firm* — Birch, Stewart, Kolasch & Birch LLP

(57) ABSTRACT

Provided is a method for inducing immunity for therapy of a cancer(s). The method includes the step of administering to an individual with cancer at least one polypeptide selected from the polypeptides (a) or (b) below, and/or a recombinant vector(s) that comprise(s) a polynucleotide(s) encoding the at least one polypeptide, the recombinant vector(s) being capable of expressing the polypeptide(s) in vivo: (a) a polypeptide in any one of the amino acid sequences of SEQ ID NOs: 2, 4, 22, or 24; and (b) a polypeptide having a sequence identity of not less than 95% to the polypeptide (a). Further, an in vitro method for preparing an antigen-presenting cell is provided. The method includes the step of contacting the antigen-presenting cell with the at least one polypeptide selected from: (a) a polypeptide in any one of the amino acid sequences of SEQ ID NOs: 2, 4, 22, or 24; and (b) a polypeptide having a sequence identity of not less than 95% to the polypeptide (a).

8 Claims, 3 Drawing Sheets
Specification includes a Sequence Listing.

(56) References Cited

OTHER PUBLICATIONS

Ariyama et al., "Decrease in Membrane Phospholipid Unsaturation Induces Unfolded Protein Response," The Journal of Biological Chemistry, vol. 285, No. 29, Jul. 16, 2010 (Published online: May 20, 2010), pp. 22027-22035.

Bansal et al., "Silencing of Stearoyl-CoA Desaturase Inhibits Proliferation and Induces Apoptosis in Human Hepatocellular Carcinoma," American Journal of Gastroenterology, vol. 103, Sep. 2008, 3 pages (S146).

Bowie et al., "Deciphering the Message in Protein Sequences: Tolerance to Amino Acid Substitutions", Science, vol. 247, pp. 1306-1310, 1990.

Extended European Search Report for European Application No. 12786721.6, dated Oct. 30, 2014.

Heppner et al., "Tumor heterogeneity: biological implication and therapeutic consequences", Cancer Metastasis Review, vol. 2, pp. 5-23, 1983.

Igal et al., "Stearoyl-CoA desaturase-1: a novel key player in the mechanisms of cell proliferation, programmed cell death and transformation to cancer," Carcinogenesis, vol. 31, No. 9, 2010, pp. 1509-1515.

International Search Report dated Jun. 26, 2012 for International Application No. PCT/JP2012/062749.

Lazar et al., "Transforming Growth Factor Alpha: Mutation of Aspartic Acid 47 and Leucine 48 Results in Different Biological Activities", Molecular Cellular Biology, vol. 8, No. 3, pp. 1247-1252, 1988.

Moore et al., "Loss of stearoyl-CoA desaturase expression is a frequent event in prostate carcinoma," International Journal of Cancer, vol. 114, 2005, pp. 563-571.

Morgan-Lappe et al., "Identification of Ras-Related Nuclear Protein, Targeting Protein for Xenopus Kinesin-like Protein 2, and Stearoyl-CoA Desaturase 1 as Promising Cancer Targets from an RNAi-Based Screen," Cancer Research, vol. 67, No. 9, May 1, 2007, pp. 4390-4398.

Sahin et al., "Human neoplasms elicit multiple specific immune responses in the autologous host," Proceedings of the National Academy of Sciences, vol. 92, Dec. 1995, pp. 11810-11813.

Scaglia et al., "High stearoyl-CoA desaturase protein and activity levels in simian virus 40 transformed-human lung fibroblasts," Biochimica et Biophysica Acta, vol. 1687, 2005 (Available online: Dec. 8, 2004), pp. 141-151.

Scaglia et al., "Inhibition of StearoylCoA Desaturase-1 Inactivates Acetyl-CoA Carboxylase and Impairs Proliferation in Cancer Cells: Role of AMPK," PLoS ONE, vol. 4, Issue 8, e6812, Aug. 27, 2009, pp. 1-14.

Van Der Bruggen et al., "A Gene Encoding an Antigen Recognized by Cytolytic T Lymphocytes on a Human Melanoma," Science, vol. 254, Dec. 13, 1991, pp. 1643-1647.

Whisstock et al., "Prediction of protein function from protein sequence and structure", Quarterly Reviews in Biophysics, vol. 36, No. 3, pp. 307-340, 2007.

Zhang et al., "201 the Scd1 Gene Functions as a Tumor Suppressor in Leukemia Stem Cells," 52th Annual Meeting of the American-Society-of-Hematology (ASH), Blood, vol. 116, No. 21, Dec. 6, 2010: 7:30 AM, 3 pages.

English translation of a Russian Office Action, dated Sep. 30, 2016, for Russian Application No. 2013156409.

Zhang et al., "Human stearoyl-CoA desaturase: alternative transcripts generated from a single gene by usage of tandem polyadenylation sites," Biochemical Journal, vol. 340, 1999, pp. 255-264.

\* cited by examiner

IMMUNITY INDUCTION AGENT

CROSS REFERENCE TO RELATED APPLICATIONS

This application is a Divisional of copending application Ser. No. 14/118,417, filed on Jan. 16, 2014, which was filed as PCT International Application No. PCT/JP2012/062749 on May 18, 2012, which claims the benefit under 35 U.S.C. § 119(a) to Patent Application No. 2011-112210, filed in Japan on May 19, 2011, all of which are hereby expressly incorporated by reference into the present application.

TECHNICAL FIELD

The present invention relates to a novel immunity-inducing agent useful as a therapeutic and/or prophylactic agent for cancer.

BACKGROUND ART

Cancer is the commonest cause for death among all of the causes for death, and therapies carried out therefor at present are mainly surgical treatment, which may be carried out in combination with radiotherapy and/or chemotherapy. In spite of the developments of new surgical methods and discovery of new anti-cancer agents in recent years, treatment results of cancers have not been improved very much so far except for some cancers. In recent years, by virtue of the development in molecular biology and cancer immunology, cancer antigens recognized by cytotoxic T cells reactive with cancers, as well as the genes encoding cancer antigens, were identified, and expectations for antigen-specific immunotherapies have been raised.

In immunotherapy, in order to reduce side effects, the peptide or protein to be recognized as the antigen needs to be hardly present in normal cells, and to be specifically present in cancer cells. In 1991, Boon et al. of Ludwig Institute in Belgium isolated a human melanoma antigen MAGE 1, which is recognized by CD8-positive T cells, by a cDNA-expression cloning method using an autologous cancer cell line and cancer-reactive T cells (Non-patent Document 1). Thereafter, the SEREX (serological identifications of antigens by recombinant expression cloning) method, wherein tumor antigens recognized by antibodies produced in the living body of a cancer patient in response to the patient's own cancer are identified by application of a gene expression cloning method, was reported (Patent Document 1, Non-patent Document 2), and several cancer antigens have been isolated by this method. Using a part of the cancer antigens as targets, clinical tests for cancer immunotherapy have started.

On the other hand, as in human, a number of tumors such as mammary gland tumor and squamous cell carcinoma are known in dogs and cats, and they rank high also in the statistics of diseases in dogs and cats. However, no therapeutic agent, prophylactic agent or diagnostic agent effective for cancers in dogs or cats exists at present. Since most tumors in dogs and cats are realized by their owners only after the tumors grew larger due to the progression, their visit to the hospital is already too late, and even if they receive surgical excision or administration of a human drug (an anticancer drug or the like), they often die shortly after the treatment. Under such circumstances, if therapeutic agents and prophylactic agents for cancer effective for dogs and cats become available, their uses for dog cancers are expected to be developed.

Stearoyl-CoA desaturase 1 (SCD1) introduces a double bond to the C9-C10 position of a saturated fatty acid. Preferred substrates for the enzyme are palmitoyl-CoA (16:0) and stearoyl-CoA (18:0), and these are converted to palmitoleoyl-CoA (16:1) and oleoyl-CoA (18:1), respectively. The obtained monounsaturated fatty acid can then be used in vivo for preparation of phospholipids, triglycerides and cholesteryl esters. Further, various cancers such as liver cancer, esophagus cancer and colon cancer show increased expression of SCD1, and it has been reported that inhibition of the function of SCD1 with siRNA or a low-molecular-weight compound causes suppression of the cell growth or induction of apoptosis (Non-patent Documents 3, 4 and 5). However, there is no report suggesting that SCD1 protein has immunity-inducing activity against cancer cells and hence that the protein is useful for treatment or prophylaxis of cancer.

PRIOR ART DOCUMENTS

Patent Document

[Patent Document 1] U.S. Pat. No. 5,698,396 B

Non-Patent Documents

[Non-patent Document 1] Bruggen P. et al., Science, 254: 1643-1647 (1991)
[Non-patent Document 2] Proc. Natl. Acad. Sci. USA, 92: 11810-11813 (1995)
[Non-patent Document 3] Scaglia N. et al., PLoS One 4: e6812 (2009)
[Non-patent Document 4] Morgan-Lappe S E. et al., Cancer Res 67: 4390-4398 (2007)
[Non-patent Document 5] Scaglia N. et al., Biochim Biophys Acta 1687: 141-151 (2005)
[Non-patent Document 6] Ariyama H. et al., J Biol Chem (2010)

SUMMARY OF THE INVENTION

Problems to be Solved by the Invention

The present invention aims to discover a novel polypeptide useful for a therapeutic and/or prophylactic agent for cancer, and to provide the polypeptide for use in an immunity-inducing agent.

Means for Solving the Problems

By the SEREX method using a dog testis-derived cDNA library and serum obtained from a tumor-bearing dog, the present inventors intensively studied to obtain a cDNA encoding a protein which binds to antibodies present in serum derived from a tumor-bearing living body, and, based on the cDNA, a polypeptide of dog stearoyl-CoA desaturase 1 (hereinafter referred to as SCD1) having the amino acid sequence of SEQ ID NO:2 was prepared. Further, based on human and mouse homologous genes of the obtained gene, human and mouse SCD1s having the amino acid sequences of SEQ ID NOs:4 and 6 were prepared. Further, the present inventors discovered that these SCD1 polypeptides are specifically expressed in tissues or cells of breast cancer, brain tumor, colon cancer, perianal adenocarcinoma, mastocytoma, neuroblastoma, renal cancer, liver cancer, lung cancer, prostate cancer and leukemia. The present inventors further discovered that administration of the SCD1 to a living body enables induction of immunocytes against SCD1 in the living body and regression of a tumor expressing SCD1 in the living body. Further, the present inventors discovered that a recombinant vector which can express a polynucleotide encoding the SCD1 polypeptide or a fragment thereof induces an antitumor effect against cancer expressing SCD1 in a living body.

Further, the present inventors discovered that an SCD1 polypeptide has a capacity to be presented by antigen-presenting cells to cause activation and the growth of cytotoxic T cells specific to the peptide (immunity-inducing activity), and therefore that the polypeptide is useful for therapy and/or prophylaxis of cancer. Further, the present inventors discovered that antigen-presenting cells which have contacted with the polypeptide, and T cells which have contacted with the antigen-presenting cells, are useful for therapy and/or prophylaxis of cancer, thereby completing the present invention.

Thus, the present invention has the following characteristics.

(1) An immunity-inducing agent comprising as an effective ingredient(s) at least one polypeptide having immunity-inducing activity selected from the polypeptides (a) to (c) below, and/or a recombinant vector(s) that comprise(s) a polynucleotide(s) encoding the at least one polypeptide, the recombinant vector(s) being capable of expressing the polypeptide(s) in vivo:

(a) a polypeptide composed of not less than 7 consecutive amino acids in any one of the amino acid sequences of SEQ ID NOs:4, 2, 22 and 24 in SEQUENCE LISTING;

(b) a polypeptide having a sequence identity of not less than 85% to the polypeptide (a) and composed of not less than 7 amino acids; and (c) a polypeptide comprising the polypeptide (a) or (b) as a partial sequence thereof.

(2) The immunity-inducing agent according to (1), wherein the polypeptide having immunity-inducing activity is a polypeptide having the amino acid sequence of SEQ ID NO:4, 2, 22 or 24 in SEQUENCE LISTING.

(3) The immunity-inducing agent according to (1) or (2), which is an agent for treating antigen-presenting cells.

(4) The immunity-inducing agent according to (1) or (2), which is a therapeutic and/or prophylactic agent for a cancer(s).

(5) The immunity-inducing agent according to (4), wherein the cancer(s) is/are a cancer(s) expressing SCD1.

(6) The immunity-inducing agent according to (4) or (5), wherein the cancer(s) is/are breast cancer, brain tumor, colon cancer, perianal adenocarcinoma, mastocytoma, neuroblastoma, renal cancer, liver cancer, lung cancer, prostate cancer and/or leukemia.

(7) The immunity-inducing agent according to any one of (1) to (6), further comprising an immunoenhancer.

(8) The immunity-inducing agent according to (7), wherein the immunoenhancer is at least one selected from the group consisting of Freund's incomplete adjuvant; Montanide; poly-I:C and derivatives thereof; CpG oligonucleotides; interleukin-12; interleukin-18; interferon-α; interferon-β; interferon-ω; interferon-γ; and Flt3 ligand.

Effect of the Invention

By the present invention, a novel immunity-inducing agent useful for therapy, prophylaxis and/or the like of cancer is provided. As concretely described in the later-mentioned Examples, administration of the polypeptide used in the present invention to a living body enables induction of immunocytes in the living body, and a cancer which has already occurred can be reduced or regressed. Therefore, the polypeptide is useful for therapy and/or prophylaxis of cancer.

BEST MODE FOR CARRYING OUT THE INVENTION

Figures 1A, 1B:
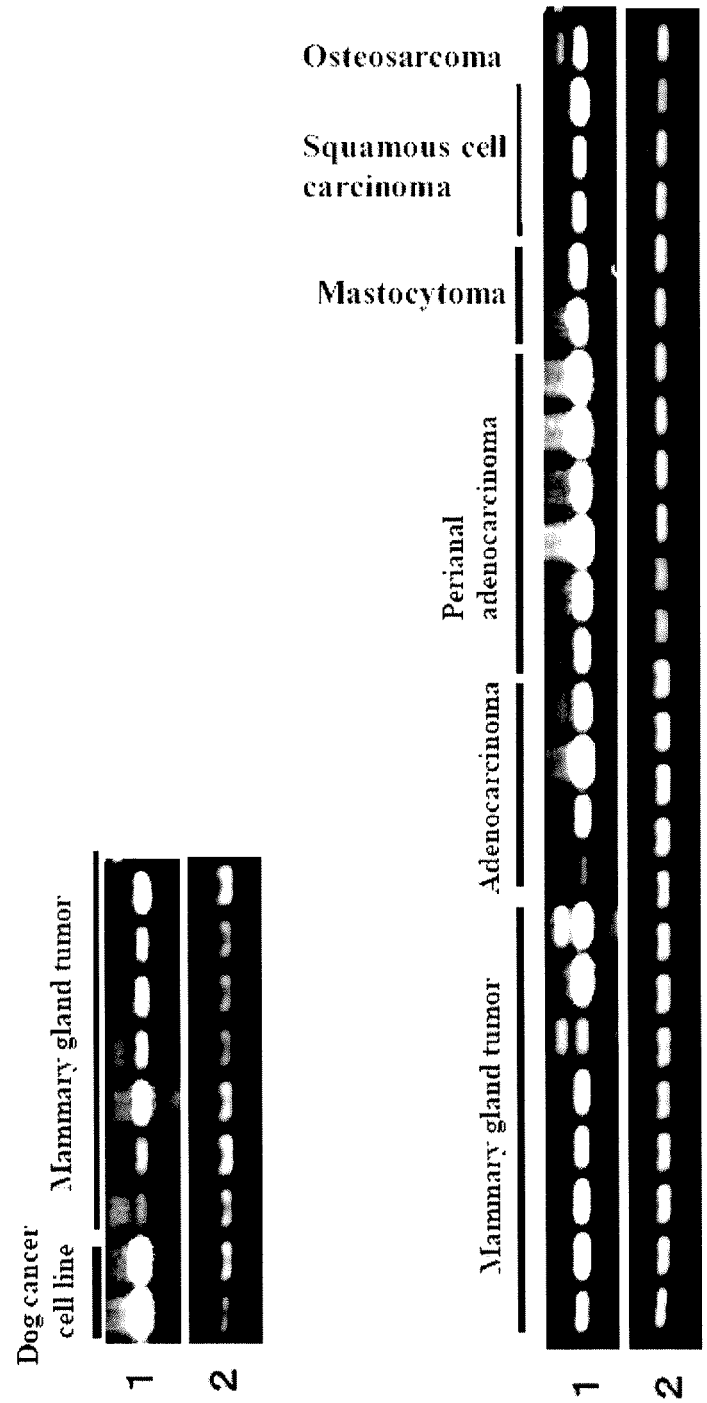
FIGS. 1A and 1B show the expression patterns of the identified SCD1 gene in dog normal tissues, tumor tissues and cancer cell lines. Reference numeral 1, the expression patterns of the dog SCD1 gene in various dog tissues and cell lines; reference numeral 2, the expression patterns of the dog GAPDH gene in various dog tissues and cell lines.

Examples of the polypeptide contained in the immunity-inducing agent of the present invention as an effective ingredient include the following. In the present invention, the term "polypeptide" means a molecule formed by a plurality of amino acids linked together by peptide bonds, and includes not only polypeptide molecules having large numbers of amino acids constituting them, but also low-molecular-weight molecules having small numbers of amino acids (oligopeptides), and full-length proteins. The present invention also includes the full-length SCD1 proteins having the amino acid sequence of SEQ ID NO:4, 2, 22 or 24.

(a) A polypeptide that is composed of not less than 7 consecutive amino acids in a polypeptide having the amino acid sequence of SEQ ID NO:4, 2, 22 or 24 in SEQUENCE LISTING, and has an immunity-inducing activity.

(b) A polypeptide composed of not less than 7 amino acids, which polypeptide has a sequence identity of not less than 85% to the polypeptide (a) and an immunity-inducing activity.

(c) A polypeptide that comprises the polypeptide (a) or (b) as a partial sequence thereof, and has an immunity-inducing activity.

In the present invention, the term "having an amino acid sequence" means that amino acid residues are arrayed in such an order. Therefore, for example, "polypeptide having the amino acid sequence of SEQ ID NO:2" means the polypeptide having the amino acid sequence of Met Pro Ala His . . . (snip) . . . Tyr Lys Ser Gly shown in SEQ ID NO:2, which polypeptide has a size of 360 amino acid residues. Further, for example, "polypeptide having the amino acid sequence of SEQ ID NO:2" may be referred to as "polypeptide of SEQ ID NO:2" for short. This also applies to the term "having a base sequence". In this case, the term "having" may be replaced with the expression "composed of".

As used herein, the term "immunity-inducing activity" means an ability to induce immunocytes that secrete cytokines such as interferon in a living body.

Whether or not the polypeptide has an immunity-inducing activity can be confirmed using, for example, the known ELISPOT assay. More specifically, for example, as described in the Examples below, cells such as peripheral blood mononuclear cells are obtained from a living body subjected to administration of the polypeptide whose immunity-inducing activity is to be evaluated, and the obtained cells are then cocultured with the polypeptide, followed by measuring the amount(s) of a cytokine(s) produced by the cells using a specific antibody/antibodies, thereby enabling measurement of the number of immunocytes among the cells. By this, evaluation of the immunity-inducing activity is possible.

Alternatively, as described in the later-mentioned Examples, administration of the recombinant polypeptide of any of (a) to (c) described above to a tumor-bearing animal allows regression of the tumor by its immunity-inducing activity. Thus, the above immunity-inducing activity can be evaluated also as an ability to suppress the growth of cancer cells or to cause reduction or disappearance of a cancer tissue (tumor) (hereinafter referred to as "antitumor activity"). The antitumor activity of a polypeptide can be confirmed by, for example, as more specifically described in the Examples below, observation of whether or not a tumor is reduced when the polypeptide was actually administered to a tumor-bearing living body.

Alternatively, the antitumor activity of a polypeptide can be evaluated also by observation of whether or not T cells stimulated with the polypeptide (that is, T cells brought into contact with antigen-presenting cells presenting the polypeptide) show a cytotoxic activity against tumor cells in vitro. The contact between the T cells and the antigen-presenting cells can be carried out by their coculture in a liquid medium, as mentioned below. Measurement of the cytotoxic activity can be carried out by, for example, the known method called $^{51}$Cr release assay described in Int. J. Cancer, 58: p 317, 1994. In cases where the polypeptide is to be used for therapy and/or prophylaxis of cancer, the evaluation of the immunity-inducing activity is preferably carried out using the antitumor activity as an index, although the index is not limited thereto.

Each of the amino acid sequences of SEQ ID NOs:2, 4, 22 and 24 in SEQUENCE LISTING disclosed in the present invention is an amino acid sequence of SCD1 that was isolated, by the SEREX method using a dog testis-derived cDNA library and serum of a tumor-bearing dog, as a polypeptide that specifically binds to an antibody existing in the serum of a tumor-bearing dog, or a homologous factor of the polypeptide in human, cow or horse (see Example 1). Human SCD1, which is the human homologous factor of dog SCD1, has a sequence identity of 89% in terms of the base sequence and 90% in terms of the amino acid sequence; bovine SCD1, which is the bovine homologous factor, has a sequence identity of 88% in terms of the base sequence and 87% in terms of the amino acid sequence; and equine SCD1, which is the equine homologous factor, has a sequence identity of 90% in terms of the base sequence and 87% in terms of the amino acid sequence.

The polypeptide (a) is a polypeptide composed of not less than 7 consecutive, preferably 8, 9 or not less than 10 consecutive, amino acids in the polypeptide having the amino acid sequence of SEQ ID NO:2, 4, 22 or 24, and has an immunity-inducing activity. The polypeptide is more preferably a polypeptide composed of an amino acid sequence having a sequence identity of not less than 85% to the amino acid sequence of SEQ ID NO:4, and the polypeptide especially preferably has the amino acid sequence of SEQ ID NO:2, 4, 22 or 24. As is known in the art, a polypeptide having not less than about 7 amino acid residues can exert its antigenicity and immunogenicity. Thus, a polypeptide having not less than 7 consecutive amino acid residues in the amino acid sequence of SEQ ID NO:2, 4, 22 or 24 can have an immunity-inducing activity, so that the polypeptide can be used for preparation of the immunity-inducing agent of the present invention.

As a principle of immune induction by administration of a cancer antigenic polypeptide, the following process is known: a polypeptide is incorporated into an antigen-presenting cell and then degraded into smaller fragments by peptidases in the cell, followed by being presented on the surface of the cell. The fragments are then recognized by a cytotoxic T cell or the like that selectively kills cells presenting the antigen. The size of the polypeptide presented on the surface of the antigen-presenting cell is relatively small and about 7 to 30 amino acids. Therefore, from the viewpoint of presenting the polypeptide on the surface of the antigen-presenting cell, one preferred mode of the above-described polypeptide (a) is a polypeptide composed of about 7 to 30 consecutive amino acids in the amino acid sequence of SEQ ID NO:2, 4, 22 or 24, and more preferably, a polypeptide composed of about 8 to 30 or about 9 to 30 amino acids is sufficient as the polypeptide (a). In some cases, these relatively small polypeptides are presented directly on the surface of antigen-presenting cells without being incorporated into the antigen-presenting cells.

Further, a polypeptide incorporated into an antigen-presenting cell is cleaved at random sites by peptidases in the cell to yield various polypeptide fragments, which are then presented on the surface of the antigen-presenting cell. Therefore, administration of a large polypeptide such as the full-length region of SEQ ID NO:2, 4, 22 or 24 inevitably causes production of polypeptide fragments by degradation in the antigen-presenting cell, which fragments are effective for immune induction via the antigen-presenting cell. Therefore, also for immune induction via antigen-presenting cells, a large polypeptide can be preferably used, and the polypeptide may be composed of not less than 30, preferably not less than 100, more preferably not less than 200, still more preferably not less than 250 amino acids. The polypeptide may be still more preferably composed of the full-length region of SEQ ID NO:2, 4, 22 or 24.

The polypeptide (b) is the same polypeptide as the polypeptide (a) except that a small number of (preferably, one or several) amino acid residues are substituted, deleted and/or inserted, which has a sequence identity of not less than 90%, preferably not less than 95%, more preferably not less than 98%, still more preferably not less than 99% or not less than 99.5% to the original sequence and has an immunity-inducing activity. It is well known in the art that, in general, there are cases where a protein antigen retains almost the same antigenicity as the original protein even if the amino acid sequence of the protein is modified such that a small number of amino acid residues are substituted, deleted and/or inserted. Therefore, since the polypeptide (b) may also exert an immunity-inducing activity, it can be used for preparation of the immunity-inducing agent of the present invention. Further, the polypeptide (b) is also preferably a polypeptide having the same amino acid sequence as the amino acid sequence of SEQ ID NO:2, 4, 22 or 24 except that one or several amino acid residues are substituted, deleted and/or inserted. As used herein, the term "several"

means an integer of 2 to 10, preferably an integer of 2 to 6, more preferably an integer of 2 to 4.

As used herein, the term "sequence identity" of amino acid sequences or base sequences means the value calculated by aligning two amino acid sequences (or base sequences) to be compared such that the number of matched amino acid residues (or bases) is maximum between the amino acid sequences (or base sequences), and dividing the number of matched amino acid residues (or the number of matched bases) by the total number of amino acid residues (or the total number of bases), which value is represented as a percentage. When the alignment is carried out, one or more gaps are inserted into one or both of the two sequences to be compared as required. Such alignment of sequences can be carried out using a well-known program such as BLAST, FASTA or CLUSTAL W. When one or more gaps are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The 20 types of amino acids constituting naturally occurring proteins may be classified into groups in each of which similar properties are shared, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in many cases, substitution of an amino acid within the same group does not change the properties of the polypeptide. Therefore, in cases where an amino acid residue in the polypeptide (a) of the present invention is substituted, the probability that the immunity-inducing activity can be maintained may be increased by carrying out the substitution within the same group, which is preferred.

The polypeptide (c) is a polypeptide that comprises the polypeptide (a) or (b) as a partial sequence and has an immunity-inducing activity. That is, the polypeptide (c) is a polypeptide in which one or more amino acids and/or one or more polypeptides is added at one or both ends of the polypeptide (a) or (b), and has an immunity-inducing activity. Such a polypeptide can also be used for preparation of the immunity-inducing agent of the present invention.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques by preparing a polynucleotide encoding the polypeptide and incorporating the polynucleotide into an expression vector, followed by introducing the resulting vector into a host cell and allowing the host cell to produce the polypeptide therein.

The polynucleotide encoding the above polypeptide can be easily prepared by a known genetic engineering technique or a conventional method using a commercially available nucleic acid synthesizer. For example, DNA having the base sequence of SEQ ID NO:1 can be prepared by carrying out PCR using a dog chromosomal DNA or cDNA library as a template, and a pair of primers designed such that the base sequence of SEQ ID NO:1 can be amplified therewith. DNA having the base sequence of SEQ ID NO:3 can be similarly prepared by using a human chromosomal DNA or cDNA library as the template. The reaction conditions for the PCR can be set appropriately, and examples of the reaction conditions include, but are not limited to, repeating the reaction process of 94° C. for 30 seconds (denaturation), 55° C. for 30 seconds to 1 minute (annealing) and 72° C. for 2 minutes (extension) for, for example, 30 cycles, followed by the reaction at 72° C. for 7 minutes. Further, the desired DNA can be isolated by preparing an appropriate probe or primer based on the information of the base sequence or the amino acid sequence of SEQ ID NO:1 or 3 in SEQUENCE LISTING in the present description, and screening a cDNA library of dog, human or the like using the probe or primer. The cDNA library is preferably prepared from cells, an organ or a tissue expressing the protein of SEQ ID NO:2 or 4. The above-described operations such as preparation of the probe or primer, construction of the cDNA library, screening of the cDNA library and cloning of the gene of interest are known to those skilled in the art, and can be carried out according to the methods described in Molecular Cloning, Second Edition; Current Protocols in Molecular Biology; and/or the like. From the thus obtained DNA, DNA encoding the polypeptide (a) can be obtained. Further, since the codons encoding each amino acid are known, the base sequence of a polynucleotide encoding a specific amino acid sequence can be easily specified. Therefore, since the base sequence of a polynucleotide encoding the polypeptide (b) or polypeptide (c) can also be easily specified, such a polynucleotide can also be easily synthesized using a commercially available nucleic acid synthesizer according to a conventional method.

The host cells are not restricted as long as the cells can express the above-described polypeptide, and examples of the cells include, but are not limited to, prokaryotic cells such as *E. coli*; and eukaryotic cells such as mammalian cultured cells including monkey kidney cells COS1 and Chinese hamster ovary cells CHO; budding yeast; fission yeast; silkworm cells; and *Xenopus laevis* egg cells.

In cases where prokaryotic cells are used as the host cells, an expression vector containing an origin that enables replication of the vector in a prokaryotic cell, promoter, ribosome binding site, DNA cloning site, terminator and/or the like is used. Examples of the expression vector for *E. coli* include the pUC system, pBluescriptll, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In such a case, the polypeptide can also be expressed as a fusion protein with another protein.

In cases where eukaryotic cells are used as the host cells, an expression vector for eukaryotic cells, comprising a promoter, splicing site, poly(A) addition site and/or the like is used as the expression vector. Examples of such an expression vector include pKA1, pCDM8, pSVK3, pMSG, pSVL, pBK-CMV, pBK-RSV, EBV vector, pRS, pcDNA3, pMSG and pYES2. Similarly to the above case, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide can be expressed as a fusion protein comprising a tag such as a His tag, FLAG tag, myc tag, HA tag or GFP.

For the introduction of the expression vector into host cells, a well-known method such as electroporation, the calcium phosphate method, the liposome method or the DEAE dextran method may be used.

Isolation and purification of the polypeptide of interest from the host cells can be carried out by a combination of known separation operations. Examples of the known separation operations include, but are not limited to, treatment with a denaturant such as urea or with a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above methods also include, as mentioned above, those in the form of a fusion protein with another arbitrary protein. Examples of such polypeptides include fusion proteins with glutathion S-transferase (GST) and fusion proteins with a His tag. Such a polypeptide in the form of a fusion protein is also included within the scope of the present invention as the above-described polypeptide (c). Further, in some cases, the polypeptide expressed in a transformed cell is modified in various ways in the cell after translation. Such a post-translationally modified polypeptide is also included within the scope of the present invention as long as it has an immunity-inducing activity. Examples of such a post-translational modification include: elimination of N-terminal methionine; N-terminal acetylation; glycosylation; limited degradation by an intracellular protease; myristoylation; isoprenylation; and phosphorylation.

As described more concretely in the later-mentioned Examples, administration of the polypeptide having an immunity-inducing activity to a tumor-bearing living body enables regression of an already existing tumor. Therefore, the immunity-inducing agent of the present invention can be used as a therapeutic and/or prophylactic agent for cancer. Further, the polypeptide having an immunity-inducing activity can be used for a method of therapy and/or prophylaxis of cancer by immune induction.

As used herein, the terms "tumor" and "cancer" mean a malignant neoplasm, and are used interchangeably In this case, the cancer to be treated is not restricted as long as SCD1 is expressed in the cancer, and the cancer is preferably breast cancer, brain tumor, colon cancer, perianal adenocarcinoma, mastocytoma, neuroblastoma, renal cancer, liver cancer, lung cancer, prostate cancer or leukemia.

The subject animal is preferably a mammal, more preferably a mammal such as a primate, pet animal, domestic animal or sport animal, especially preferably human, dog or cat.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of cancer, it may be administered to a regional lymph node in the vicinity of the tumor to be treated, as described in the Examples below, in order to enhance its anticancer activity. The dose may be any dose as long as the dose is effective for immune induction, and, for example, in cases where the agent is used for therapy and/or prophylaxis of cancer, the dose may be one effective for therapy and/or prophylaxis of the cancer. The dose effective for therapy and/or prophylaxis of cancer is appropriately selected depending on the size, symptoms and the like of the tumor, and the effective dose is usually 0.0001 μg to 1000 μg, preferably 0.001 μg to 1000 μg per subject animal per day. The agent may be administered once, or dividedly in several times. The agent is preferably administered dividedly in several times, every several days to several months. As concretely shown in the Examples below, the immunity-inducing agent of the present invention can cause regression of an already occurred tumor. Therefore, since the agent can exert its anticancer activity also against a small number of cancer cells at an early stage, development or recurrence of cancer can be prevented by using the agent before development of the cancer or after therapy for the cancer. That is, the immunity-inducing agent of the present invention is effective for both therapy and prophylaxis of cancer.

The immunity-inducing agent of the present invention may contain only a polypeptide or may be formulated by being mixed as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additives include, but are not limited to, diluents such as physiological buffer solutions; vehicles such as sugar, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the immunoenhancer include adjuvants. Adjuvants can enhance the immune response by providing a reservoir of antigen (extracellularly or inside macrophages), activating macrophages and stimulating specific sets of lymphocytes, thereby enhancing the immune response and hence the anticancer action. Therefore, especially in cases where the immunity-inducing agent of the present invention is used for therapy and/or prophylaxis of cancer, the immunity-inducing agent preferably comprises an adjuvant, in addition to the above-described polypeptide as an effective ingredient. Many types of adjuvants are well known in the art, and any of these adjuvants may be used. Specific examples of the adjuvants include MPL (SmithKline Beecham), homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in PCT application WO 96/33739 (SmithKline Beecham); QS-7, QS-17, QS-18 and QS-L1 (So and 10 colleagues, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 colleagues, Nature, Vol. 374, p. 546-549); poly-I.C and derivatives thereof (e.g., poly ICLC); and various water-in-oil emulsions prepared from biodegradable oils such as squalene and/or tocopherol. Among these, Freund's incomplete adjuvant; Montanide; poly-I.C and derivatives thereof; and CpG oligonucleotides are preferred. The mixing ratio between the above-described adjuvant and the polypeptide is typically about 1:10 to 10:1, preferably about 1:5 to 5:1, more preferably about 1:1. However, the adjuvant is not limited to the above-described examples, and adjuvants known in the art other than those described above may also be used when the immunity-inducing agent of the present invention is administered (see, for example, Goding, "Monoclonal Antibodies: Principles and Practice, 2nd edition", 1986). Preparation methods for mixtures or emulsions of a polypeptide and an adjuvant are well known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples of the cytokines include, but are not limited to, interleukin-12 (IL-12), GM-CSF, IL-18, interferon-α, interferon-β, interferon-ω, interferon-γ, and Flt3 ligand, which have been shown to enhance the prophylactic action of vaccines. Such factors may also be used as the above-described immunoenhancer, and may be contained in the immunity-inducing agent of the present invention, or may be prepared as a separate composition to be administered to a patient in combination with the immunity-inducing agent of the present invention.

By bringing the above-described polypeptide into contact with antigen-presenting cells in vitro, the antigen-presenting cells can be made to present the polypeptide. That is, the polypeptides (a) to (c) described above can be used as agents for treating antigen-presenting cells. Examples of the antigen-presenting cells which may be preferably used include dendritic cells and B cells having MHC class I molecules. Various MHC class I molecules have been identified and are well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

By administering an effective amount of such dendritic cells, a response desired for therapy of a cancer can be induced. As the cells, bone marrow or umbilical cord blood donated by a healthy individual, or bone marrow, peripheral blood or the like of the patient may be used. When autologous cells of the patient are used, high safety can be attained and serious side effects are expected to be avoided. The peripheral blood or bone marrow may be any of a fresh sample, cold-stored sample and cryopreserved sample. As for the peripheral blood, whole blood may be cultured or the leukocyte components alone may be separated and cultured, and the latter is more efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. The production method for the cytokine is not restricted, and a naturally-occurring or recombinant cytokine or the like may be employed as long as its safety and physiological activity have been confirmed. Preferably, a preparation with assured quality for medical use is used in the minimum necessary amount. The concentration of the cytokine(s) to be added is not restricted as long as the dendritic cells are induced at the concentration, and usually, the total concentration of the cytokine(s) is preferably about 10 to 1000 ng/mL, more preferably about 20 to 500 ng/mL. The culture may be carried out using a well-known medium usually used for culture of leukocytes. The culturing temperature is not restricted as long as proliferation of leukocytes is possible at the temperature, and a temperature of about 37° C., which is the body temperature of human, is most preferred. The atmospheric environment during the culture is not restricted as long as proliferation of the leukocytes is possible under the environment, and the culture is preferably performed under a flow of 5% $CO_2$. The culturing period is not restricted as long as a necessary number of the cells are induced, and usually 3 days to 2 weeks. As for the apparatuses used for separation and culturing of the cells, appropriate apparatuses, preferably those whose safety upon application to medical uses have been confirmed and whose operations are stable and simple, may be employed. In particular, examples of the cell-culturing apparatus include not only general vessels such as Petri dishes, flasks and bottles, but also layer-type vessels, multistage vessels, roller bottles, spinner-type bottles, bag-type culturing vessels and hollow fiber columns.

The method per se to be used for bringing the above-described polypeptide into contact with the antigen presenting cells in vitro may be those well known in the art. For example, the antigen-presenting cells may be cultured in a culture medium containing the above-described polypeptide. The concentration of the peptide in the medium is not restricted, and usually about 1 to 100 µg/ml, preferably about 5 to 20 µg/ml. The cell density during the culture is not restricted and usually about $10^3$ to $10^7$ cells/ml, preferably about $5×10^4$ to $5×10^6$ cells/ml. The culture is preferably carried out according to a conventional method at 37° C. under the atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues, although the length is not restricted.

By culturing the antigen-presenting cells in the coexistence of the above-described polypeptide, the polypeptide is incorporated into MHC molecules of the antigen-presenting cells and presented on the surface of the antigen-presenting cells. Therefore, using the above-described polypeptide, isolated antigen-presenting cells containing the complex between the polypeptide and the MHC molecule can be prepared. Such antigen-presenting cells can present the polypeptide against T cells in vivo or in vitro, to induce, and allow proliferation of, cytotoxic T cells specific to the polypeptide.

By bringing the thus prepared antigen-presenting cells having the complex between the above-described polypeptide and the MHC molecule into contact with T cells in vitro, cytotoxic T cells specific to the polypeptide can be induced and allowed to proliferate. This may be carried out by coculturing the above-described antigen-presenting cells and T cells in a liquid medium. For example, the antigen-presenting cells may be suspended in a liquid medium and placed in a vessel such as a well of a microplate, followed by adding T cells to the well and then performing culture. The mixing ratio of the antigen-presenting cells to the T cells in the coculture is not restricted, and usually about 1:1 to 1:100, preferably about 1:5 to 1:20 in terms of the cell number. The density of the antigen-presenting cells to be suspended in the liquid medium is not restricted, and usually about 100 to 10,000,000 cells/ml, preferably about 10,000 to 1,000,000 cells/ml. The coculture is preferably carried out by a conventional method at 37° C. under the atmosphere of 5% $CO_2$. The culturing period is not restricted, and usually 2 days to 3 weeks, preferably about 4 days to 2 weeks. The coculture is preferably carried out in the presence of one or more interleukins such as IL-2, IL-6, IL-7 and/or IL-12. In such cases, the concentration of IL-2 or IL-7 is usually about 5 to 20 U/ml, the concentration of IL-6 is usually about 500 to 2000 U/ml, and the concentration of IL-12 is usually about 5 to 20 ng/ml, but the concentrations of the interleukins are not restricted thereto. The above coculture may be repeated once to several times with addition of fresh antigen-presenting cells. For example, the operation of discarding the culture supernatant after the coculture and adding a fresh suspension of antigen-presenting cells to further conduct the coculture may be repeated once to several times. The conditions for each coculture may be the same as those described above.

By the above-described coculture, cytotoxic T cells specific to the polypeptide are induced and allowed to proliferate. Thus, using the above-described polypeptide, isolated T cells can be prepared which selectively bind to the complex between the polypeptide and the MHC molecule.

As described in the Examples below, the SCD1 gene is expressed specifically in breast cancer cells, breast cancer tissues, brain tumor cells, brain tumor tissues, colon cancer cells, colon cancer tissues, perianal adenocarcinoma tissues, perianal adenocarcinoma cells, mastocytoma tissues, mastocytoma cells, neuroblastoma cells, renal cancer cells, renal cancer tissues, liver cancer cells, liver cancer tissues, lung cancer cells, lung cancer tissues, prostate cancer cells, prostate cancer tissues and leukemia cells. Therefore, it is thought that, in these cancer species, a significantly larger amount of SCD1 exists than in normal cells. When the thus prepared cytotoxic T cells are administered to a living body such that a part of the SCD1 polypeptide present in cancer cells is presented by MHC molecules on the surface of the cancer cells, the cytotoxic T cells can damage the cancer cells using the presented polypeptide as a marker. Since the antigen-presenting cells presenting a part of the above-described SCD1 polypeptide can induce, and allow proliferation of cytotoxic T cells specific to the polypeptide also in vivo, cancer cells can be damaged also by administering the antigen-presenting cells to a living body. That is, the cytotoxic T cells and the antigen-presenting cells prepared using the polypeptide are also effective as therapeutic and/or prophylactic agents for cancer, similarly to the immunity-inducing agent of the present invention.

In cases where the above-described isolated antigen-presenting cells or isolated T cells are administered to a living body, these are preferably prepared by treating antigen presenting cells or T cells collected from the patient to be treated, using the polypeptide (a), (b) or (c) as described above in order to avoid the immune response in the living body that attacks these cells as foreign bodies.

The therapeutic and/or prophylactic agent for cancer comprising as an effective ingredient the antigen-presenting cells or T cells is preferably administered via a parenteral administration route, for example, by intravenous or intraarterial administration. The dose is appropriately selected depending on the symptoms, the purpose of administration and the like, and is usually 1 cell to 10,000,000,000,000 cells, preferably 1,000,000 cells to 1,000,000,000 cells, which dose is preferably administered once every several days to once every several months. The formulation may be, for example, the cells suspended in physiological buffered saline, and the formulation may be used in combination with another/other anticancer preparation(s) and/or cytokine(s). Further, one or more additives well known in the field of formulation of pharmaceuticals may also be added.

Also by expressing a polynucleotide encoding any of the polypeptides (a) to (c) in the body of the subject animal, antibody production and cytotoxic T cells can be induced in the living body, and an effect comparable to that obtained in the case of administration of the polypeptide can be obtained. That is, the immunity-inducing agent of the present invention may be one comprising as an effective ingredient a recombinant vector having a polynucleotide encoding any of the polynucleotides (a) to (c), which recombinant vector is capable of expressing the polypeptide in a living body. Such a recombinant vector capable of expressing an antigenic polypeptide as shown in the later-mentioned Examples is also called a gene vaccine.

The vector used for production of the gene vaccine is not restricted as long as it is a vector capable of expressing the polypeptide in a cell of the subject animal (preferably in a mammalian cell), and may be either a plasmid vector or a virus vector, and any known vector in the field of gene vaccines may be used. The polynucleotide such as DNA or RNA encoding the above-described polypeptide can be easily prepared as mentioned above by a conventional method. Incorporation of the polynucleotide into the vector can be carried out using a method well known to those skilled in the art.

The administration route of the gene vaccine is preferably a parenteral route such as intramuscular, subcutaneous, intravenous or intraarterial administration. The dose may be appropriately selected depending on the type of the antigen and the like, and is usually about 0.1 μg to 100 mg, preferably about 1 μg to 10 mg in terms of the weight of the gene vaccine per kg body weight.

Examples of the method using a virus vector include those wherein a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), and the liposome method, lipofectin method, microinjection method, calcium phosphate method and electroporation method. The DNA vaccine method and liposome method are especially preferred.

Methods for making the gene encoding the above-described polypeptide used in the present invention actually act as a pharmaceutical include in vivo methods wherein the gene is directly introduced into the body, and ex vivo methods wherein a certain kind of cells are collected from the subject animal and the gene is then introduced into the cells ex vivo, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these literatures, and the like). The in vivo methods are more preferred.

In cases where the gene is administered by an in vivo method, the gene may be administered through an appropriate administration route depending on the disease to be treated, symptoms and the like. The gene may be administered by, for example, intravenous, intraarterial, subcutaneous or intramuscular administration. In cases where the gene is administered by an in vivo method, the gene may be formulated into a preparation such as a solution, and in general, it is formulated into an injection solution or the like containing DNA encoding the above-described peptide of the present invention as an effective ingredient. A commonly used carrier may be also added thereto as required. In cases of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence of SEQ ID NO:1" includes not only the actual base sequence of SEQ ID NO:1, but also the sequence complementary thereto. Thus, "the polynucleotide having the base sequence of SEQ ID NO:1" includes the single-stranded polynucleotide having the actual base sequence of SEQ ID NO:1, the single-stranded polynucleotide having the base sequence complementary thereto, and the double-stranded polynucleotide composed of these single-stranded polynucleotides. When a polynucleotide encoding the polypeptide used in the present invention is prepared, any one of these base sequences is appropriately selected, and those skilled in the art can easily carry out the selection.

EXAMPLES

The present invention will now be described more concretely by way of Examples.

Example 1: Obtaining Novel Cancer Antigen Protein by SEREX Method (1) Preparation of cDNA Library Total RNA was extracted from testis of a dog by the acid-guanidium-phenol-chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 µg), a cDNA phage library was synthesized. For the preparation of a cDNA phage library, cDNA Synthesis Kit, Zap-cDNA Synthesis Kit, and ZAP-cDNA Gigapack III Gold Cloning Kit (manufactured by STRATAGENE) were used in accordance with the protocols attached to the kits. The size of the prepared cDNA phage library was $1 \times 10^6$ pfu/ml.

(2) Screening of cDNA Library with Serum

Using the thus prepared cDNA phage library, immunoscreening was carried out. More specifically, the host $E.$ $coli$ (XL1-Blue MRF') was infected with the library such that 2340 clones appeared on an NZY agarose plate with a size of 90 mm dia.×15 mm, and cultured at 42° C. for 3 to 4 hours to allow the phage to form plaques. The plate was covered with a nitrocellulose membrane (Hybond C Extra: manufactured by GE Healthcare Bio-Science) impregnated with IPTG (isopropyl-β-D-thiogalactoside) at 37° C. for 4 hours to allow induction and expression of proteins, and the proteins were transferred onto the membrane. Subsequently, the membrane was recovered and soaked in TBS (10 mM Tris-HCl, 150 mM NaCl; pH 7.5) supplemented in 0.5% non-fat dry milk. The membrane was then shaken at 4° C. overnight to suppress non-specific reactions. This filter was then allowed to react with 500-fold diluted dog patient serum at room temperature for 2 to 3 hours.

As the above-described dog patient serum, serum collected from a dog patient with a perianal tumor was used. The serum was stored at −80° C. and pretreated immediately before use. The method of the pretreatment of serum was as follows. That is, the host $E.$ $coli$ (XL1-Blue MRF') was infected with λ ZAP Express phage having no foreign gene inserted, and then cultured on NZY plate medium at 37° C. overnight. Subsequently, 0.2 M NaHCO$_3$ buffer (pH 8.3) supplemented with 0.5 M NaCl was added to the plate, and the plate was left to stand at 4° C. for 15 hours, followed by collecting the supernatant as an $E.$ $coli$/phage extract. Thereafter, the collected $E.$ $coli$/phage extract was passed through an NHS-column (manufactured by GE Healthcare Bio-Science) to immobilize proteins derived from the $E.$ $coli$/phage thereon. The serum from the dog patient was passed through, and reacted with, this protein-immobilized column to remove antibodies that adsorb to $E.$ $coli$ and/or the phage. The serum fraction that passed through the column was 500-fold diluted with TBS supplemented with 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and reacted with goat anti-dog IgG (Goat anti Dog IgG-h+I HRP conjugated: manufactured by BETHYL Laboratories) 5,000-fold diluted with TBS supplemented with 0.5% non-fat dry milk as a secondary antibody at room temperature for 1 hour, followed by detection by enzyme coloring reaction using an NBT/BCIP reaction solution (manufactured by Roche). Colonies at positions corresponding to coloring-reaction-positive sites were recovered from the NZY agarose plate having a size of 90 mm dia.×15 mm, and dissolved in 500 µl of SM buffer (100 mM NaCl, 10 mM MgClSO$_4$, 50 mM Tris-HCl, 0.01% gelatin; pH 7.5). The screening was repeated as the second and third screening in the same manner as described above until a single coloring-reaction-positive colony was obtained. The isolation of the single positive clone was achieved after screening of 9110 phage clones reactive with IgG in the serum.

(3) Sequence Homology Search of Isolated Antigen Gene

To subject the single positive clone isolated by the above-described method to base sequence analysis, an operation of conversion of the phage vector to a plasmid vector was carried out. More specifically, 200 µl of a solution prepared such that the host $E.$ $coli$ (XL1-Blue MRF') was contained at an absorbance OD$_{600}$ of 1.0 was mixed with 100 µl of a purified phage solution and further with 1 µl of ExAssist helper phage (manufactured by STRATAGENE), and the reaction was then allowed to proceed at 37° C. for 15 minutes. This was followed by addition of 3 ml of LB medium to the reaction mixture, and culture was performed with the resulting mixture at 37° C. for 2.5 to 3 hours. The resulting culture was immediately incubated in a water bath at 70° C. for 20 minutes. The culture was then centrifuged at 4° C. at 1,000×g for 15 minutes, and the supernatant was recovered as a phagemid solution. Subsequently, 200 µl of a solution prepared such that the phagemid host *E. coli* (SOLR) was contained at an absorbance $OD_{600}$ of 1.0 was mixed with 10 µl of a purified phage solution, and the reaction was allowed to proceed at 37° C. for 15 minutes. Thereafter, 50 µl of the reaction mixture was plated on LB agar medium supplemented with ampicillin (final concentration: 50 µg/ml), and culture was performed at 37° C. overnight. A single colony of transformed SOLR was recovered and cultured in LB medium supplemented with ampicillin (final concentration: 50 µg/ml) at 37° C., followed by purification of plasmid DNA having the insert of interest using QIAGEN plasmid Miniprep Kit (manufactured by Qiagen).

The purified plasmid was subjected to analysis of the full-length sequence of the insert by the primer walking method using the T3 primer of SEQ ID NO:7 and the T7 primer of SEQ ID NO:8. By this sequence analysis, the gene sequence of SEQ ID NO:1 was obtained. Using the base sequence and the amino acid sequence of this gene, homology search against known genes was carried out using a sequence homology search program BLAST. As a result, it was revealed that the obtained gene is the SCD1 gene. Human SCD1, which is a human homologous factor of dog SCD1, had a sequence identity of 89% in terms of the base sequence and 90% in terms of the amino acid sequence; mouse SCD1, which is a mouse homologous factor, had a sequence identity of 84% in terms of the base sequence and 84% in terms of the amino acid sequence. The base sequence and the amino acid sequence of human SCD1 are shown in SEQ ID NO:3 and SEQ ID NO:4, respectively, and the base sequence and the amino acid sequence of mouse SCD1 are shown in SEQ ID NO:5 and SEQ ID NO:6, respectively.

(4) Analysis of Expression in Various Tissues

Figures 2A, 2B:
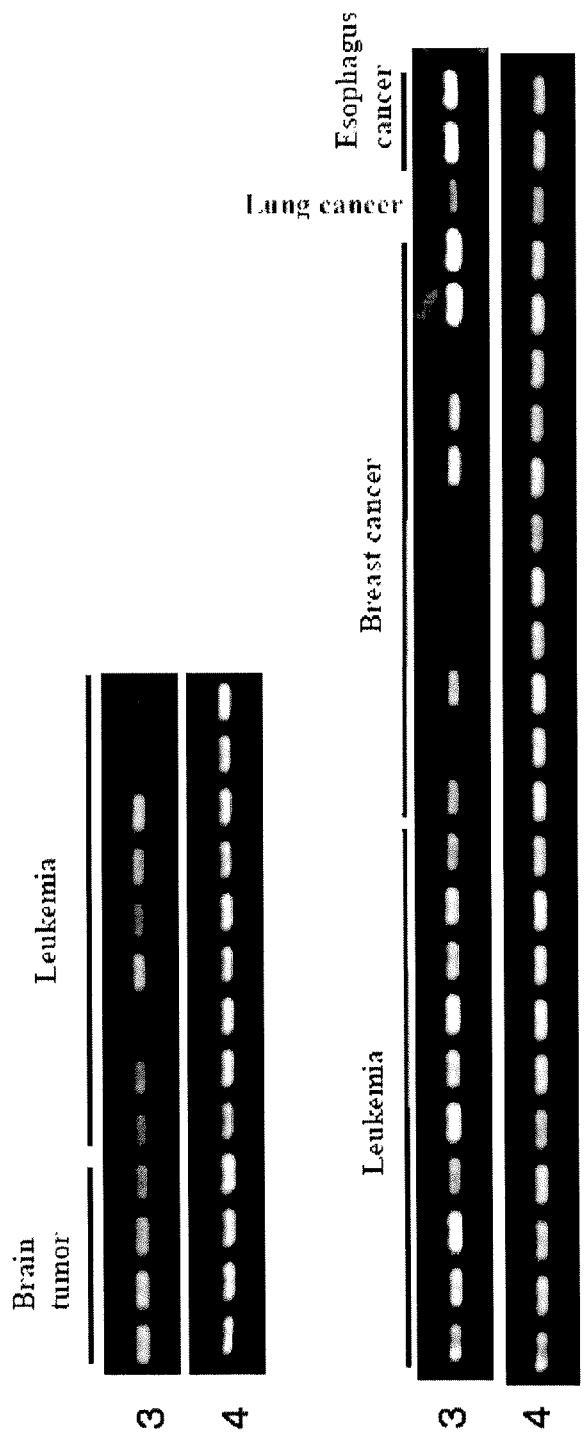
FIGS. 2A and 2B show the expression patterns of the identified SCD1 gene in human normal tissues, tumor tissues and cancer cell lines. Reference numeral 3, the expression patterns of the human SCD1 gene in various human tissues and cell lines; reference numeral 4, the expression patterns of the human GAPDH gene in various human tissues and cell lines.
Figure 3:
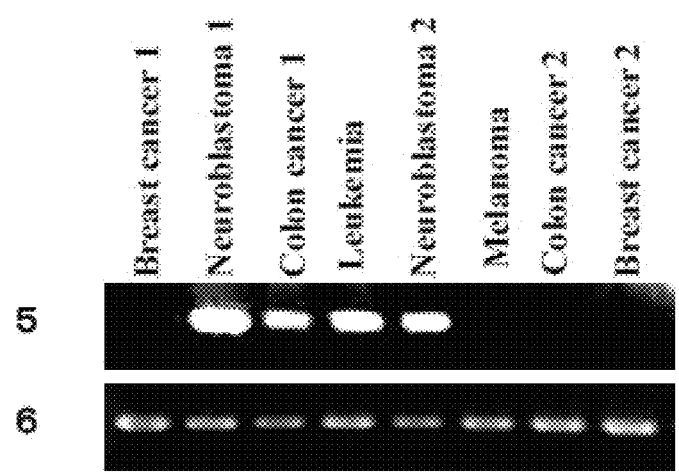
FIG. 3 shows the expression patterns of the identified SCD1 gene in mouse normal tissues, tumor tissues and cancer cell lines. Reference numeral 5, the expression patterns of the mouse SCD1 gene in various mouse tissues and cell lines; reference numeral 6, the expression patterns of the mouse GAPDH gene in various mouse tissues and cell lines.

Expression of the genes obtained by the above method in dog, human and mouse normal tissues and various cell lines were investigated by the RT-PCR (Reverse Transcription-PCR) method. The reverse transcription reaction was carried out as follows. That is, from 50 to 100 mg of each tissue or $5×10^6$ to $10×10^6$ cells of each cell line, total RNA was extracted using the TRIZOL™ reagent (manufactured by Invitrogen) (a monophasic solution of phenol, guanidine isothiocyanate, and other components which facilitate the isolation of a variety of RNA species of large or small molecular size) according to the protocol described in the attached instructions. Using this total RNA, cDNA was synthesized with the SUPERSCRIPT™ First-Strand Synthesis System for RT-PCR (manufactured by Invitrogen) (to synthesize first-strand cDNA from purified poly(A)+ or total RNA using the following: Oligo(dT)12-18 (0.5 µg/µl), Random hexamers (50 ng/µl), 10×RT buffer (20 mM Tris-HCl, pH 8.4, 500 mM KCl, 25 mM $MgCl_2$), 25 mM Magnesium Chloride, 0.1 M DTT, 10 mM dNTP mix, SUPERSCRIPT™ II RT (Reverse Transcriptase) (50 U/µl), RNASEOUT™ (40 U/µl) (Recombinant Ribonuclease Inhibitor), *E. coli* RNase H (2 U/µl), DEPC-treated water, Control RNA (50 ng/µl), Control Primer A (10 µM), Control Primer B (10 µM)) according to the protocol described in the attached instructions. As the cDNAs of human normal tissues (brain, hippocampus, testis, colon and *placenta*), Gene Pool cDNA (manufactured by Invitrogen), QUICK-CLONE™ cDNA (manufactured by CLONETECH) (double-stranded cDNA, purified to remove interfering RNA and genomic DNA) and Large-Insert cDNA Library (manufactured by CLONETECH) were used. The PCR reaction was carried out using primers specific to the obtained gene (the dog primers shown in SEQ ID NOs:9 and 10, the human primers shown in SEQ ID NOs:11 and 12, and the mouse primers shown in SEQ ID NOs:13 and 14) as described below. That is, the reagents and the attached buffer were mixed such that 0.25 µl of the sample prepared by the reverse transcription reaction, 2 µM each of the above primers, 0.2 mM each of dNTPs, and 0.65 U ExTaq polymerase (manufactured by Takara Shuzo Co., Ltd.) were contained in the resulting mixture in a final volume of 25 and the reaction was carried out by 30 cycles of 94° C. for 30 seconds, 55° C. for 30 seconds and 72° C. for 1 minute using a Thermal Cycler (manufactured by BIO RAD). As a control for comparison, primers specific to GAPDH (the dog and human GAPDH primers are shown in SEQ ID NOs:15 and 16; and the mouse GAPDH primers are shown in SEQ ID NOs:17 and 18) were used at the same time. As a result, as shown in FIG. 1, the dog SCD1 gene was not expressed in most of the healthy dog tissues, while the gene was strongly expressed in the dog tumor tissues. Also in terms of the human and mouse SCD1 genes, the expression was not observed in most of the normal human and mouse tissues, while the expression was detected in most of the cancer cell lines (FIGS. 2 and 3), as in the case of the dog SCD1 gene.

(5) Quantitative Analysis of Expression in Various Tissues

The gene obtained by the above method was subjected to investigation of expression in human normal tissues by the quantitative RT-PCR (Reverse Transcription-PCR) method. As cDNAs for human normal tissues and cancer tissues, Tissue scan Real Time cancer survey Panel I (manufactured by ORIGENE) was used. The quantitative RT-PCR was carried out using CFX96 Real Time Cystem—C1000 Thermal Cycler, manufactured by Bio-Rad Laboratories, Inc. The PCR reaction was carried out as follows using primers specific to the obtained gene (shown in SEQ ID NOs:11 and 12). That is, 5 µl of the cDNA sample, 2 µM each of the primers, and the reagents and the buffer contained in 2×SYBR Premix Ex TaqII polymerase (manufactured by Takara Shuzo Co., Ltd.) were mixed together to prepare a mixture in a final volume of 20 and the reaction was carried out by 30 cycles of 94° C. for 30 seconds, 55° C. for 30 seconds and 72° C. for 1 minute. As a result, the expression level of the SCD1 gene in each of breast cancer, colon cancer, renal cancer, liver cancer, prostate cancer and lung cancer was not less than 4 times higher than the expression level in its corresponding normal tissue. Based on these results, it can be expected that there is no concern of occurrence of side effects by antitumor agents targeting human SCD1 in normal tissues at all, and that the benefit of the pharmacological effect of the agents largely exceeds the risk of their side effects.

Example 2: Analysis of Cancer Antigenicity of SCD1 In Vivo (1) Preparation of Recombinant Vector that Expresses SCD1 In Vivo Based on the base sequence of SEQ ID NO:5, a recombinant vector that expresses SCD1 in vivo was prepared. PCR was prepared from the mouse cancer cell line N2a (purchased from ATCC), which showed the expression in Example 1. The reagents and the attached buffer were mixed such that 1 µl of the cDNA, 0.4 µM each of two kinds of primers having the HindIII and XbaI restriction sites (shown in SEQ ID NOs:19 and 20), 0.2 mM dNTP and 1.25 U PrimeSTAR HS polymerase (manufactured by Takara Shuzo Co., Ltd.) were contained in the resulting mixture in a final volume of 50 µl, and PCR was carried out by 30 cycles of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence of SEQ ID NO:5. After the PCR, the amplified DNA was subjected to electrophoresis using 1% agarose gel, and a DNA fragment of about 1000 bp was purified using QIAQUICK™ Gel Extraction Kit (manufactured by QIAGEN) (a silica membrane assembly for binding of DNA in high-salt buffer and elution with low-salt buffer or water).

The purified DNA fragment was ligated into a cloning vector pCR-Blunt (manufactured by Invitrogen). *E. coli* was transformed with the resulting ligation product, and the plasmid was then recovered. The sequence of the amplified gene fragment was confirmed to be the same as the sequence of interest by sequencing. The plasmid having the sequence of interest was treated with restriction enzymes HindIII and XbaI, and purified using QIAQUICK™ Gel Extraction Kit (a silica membrane assembly for binding of DNA in high-salt buffer and elution with low-salt buffer or water), followed by inserting the gene sequence of interest into a mammalian expression vector pcDNA3.1 (manufactured by Invitrogen) that had been treated with the restriction enzymes HindIII and XbaI. Use of this vector enables production of SCD1 protein in mammalian cells.

To 100 µg of the thus prepared plasmid DNA, 50 µg of gold particles (manufactured by Bio Rad), 100 µl of spermidine (manufactured by SIGMA) and 100 µl of 1 M $CaCl_2$ (manufactured by SIGMA) were added, and the resulting mixture was stirred by vortexing, followed by leaving the mixture to stand for 10 minutes at room temperature (the resulting particles are hereinafter referred to as the gold-DNA particles). The mixture was then centrifuged at 3000 rpm for 1 minute and the supernatant was discarded, followed by rinsing the precipitate 3 times with 100% ethanol (manufactured by WAKO). To the gold-DNA particles, 6 ml of 100% ethanol was added, and the resulting mixture was sufficiently stirred by vortexing, followed by pouring the gold-DNA particles into Tefzel Tubing (manufactured by Bio Rad) and allowing the particles to precipitate on the wall surface. Ethanol was removed by air-drying from the Tefzel Tubing to which the gold-DNA particles were attached, and the tube was then cut into pieces having a length that is appropriate for a gene gun.

(2) Antitumor Effect of SCD1 by DNA Vaccine Method

The above prepared tube was fixed in a gene gun, and the DNA vaccine was transdermally administered, by application of a pressure of 400 psi using pure helium gas, a total of 3 times at intervals of 7 days to the abdominal cavity of each of 10 individuals of A/J mice (7 weeks old, male, purchased from Japan SLC) and Balb/c mice (7 weeks old, male, purchased from Japan SLC) whose hair had been shaved (this corresponds to inoculation of 2 µg/individual of the plasmid DNA). Thereafter, a mouse neuroblastoma cell line N2a or a colon cancer cell line CT26 was transplanted to each mouse in an amount of $1 \times 10^6$ cells to evaluate the antitumor effect (prophylactic model). For each model, plasmid DNA containing no SCD1 gene inserted was administered to 10 individuals of mice to provide a control.

The antitumor effect was evaluated based on the size of the tumor (major axis×minor $axis^2/2$) and the ratio of living mice. As a result of this study, in the prophylactic model using the neuroblastoma cell line, the size of the tumor became 2966 $mm^3$ and 759 $mm^3$ on Day 43 in the control group and the SCD1 plasmid-administered group, respectively. Thus, remarkable regression of the tumor was observed in the SCD1 plasmid-administered group. Further, as a result of observation of survival in the prophylactic model using the neuroblastoma cell line, it was found that all cases died by Day 74 after the administration in the control group, while 60% of the mice survived in the SCD1 plasmid-administered group. These results indicate a significant antitumor effect in the SCD1 plasmid-administered group as compared to the control group. Similarly, in the prophylactic model using the colon cancer cell line, the size of the tumor became 2518 $mm^3$ and 604 $mm^3$ on Day 33 in the control group and the SCD1 plasmid-administered group, respectively. Thus, remarkable regression of the tumor was observed in the SCD1 plasmid-administered group. Further, as a result of observation of survival, it was found that all cases died by Day 54 after the administration in the control group, while 50% of the mice survived in the SCD1 plasmid-administered group. These results indicate a significant antitumor effect in the SCD1 plasmid-administered group as compared to the control group.

Example 3: Preparation of Human Recombinant SCD1 Protein and Evaluation of its Immunity-Inducing Ability (1) Preparation of Human Recombinant SCD1 Protein Based on the base sequence of SEQ ID NO:3, a recombinant protein of human SCD1 was prepared. The regents and the attached buffer were mixed such that 1 µl of the cDNA prepared in Example 1 whose expression could be confirmed for cDNAs from various tissues and cells by the RT-PCR method, 0.4 µM each of two kinds of primers having the EcoRI and XhoI restriction sites (shown in SEQ ID NOs:25 and 26), 0.2 mM dNTP and 1.25 U PrimeSTAR HS polymerase (manufactured by Takara Shuzo Co., Ltd.) were contained in the resulting mixture in a final volume of 50 µl, and PCR was carried out by 30 cycles of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence of SEQ ID NO:4. After the PCR, the amplified DNA was subjected to electrophoresis using 1% agarose gel, and a DNA fragment of about 1000 bp was purified using QIAQUICK™ Gel Extraction Kit (manufactured by QIAGEN) (a silica membrane assembly for binding of DNA in high-salt buffer and elution with low-salt buffer or water).

The purified DNA fragment was ligated into a cloning vector pCR-Blunt (manufactured by Invitrogen). *E. coli* was transformed with the resulting ligation product, and the plasmid was then recovered. The sequence of the amplified gene fragment was confirmed to be the same as the sequence of interest by sequencing. The plasmid having the sequence of interest was treated with restriction enzymes EcoRI and XhoI, and purified using QIAQUICK™ Gel Extraction Kit (a silica membrane assembly for binding of DNA in high-salt buffer and elution with low-salt buffer or water), followed by inserting the gene sequence of interest into an expression vector for *E. coli*, pET30a (manufactured by Novagen) that had been treated with the restriction enzymes EcoRI and XhoI. Use of this vector enables production of a His tag-fused recombinant protein. *E. coli* for expression, BL21 (DE3), was transformed with this plasmid, and expression was induced with 1 mM IPTG, to allow expression of the protein of interest in *E. coli*.

(2) Purification of Recombinant SCD1 Protein

The thus obtained recombinant *E. coli* that expresses SEQ ID NO:4 was cultured in LB medium supplemented with 100 μg/ml ampicillin at 37° C. until the absorbance at 600 nm reached about 0.7, and isopropyl-β-D-1-thiogalactopyranoside was then added to the culture at a final concentration of 1 mM, followed by further culturing the recombinant *E. coli* at 37° C. for 4 hours. Subsequently, the bacterial cells were collected by centrifugation at 4,800 rpm for 10 minutes. The pellet of the bacterial cells was suspended in phosphate-buffered saline and further subjected to centrifugation at 4,800 rpm for 10 minutes, to wash the bacterial cells.

The bacterial cells were suspended in 50 mM Tris-HCl buffer (pH 8.0) and subjected to sonication on ice. The liquid obtained by the sonication of *E. coli* was centrifuged at 6000 rpm for 20 minutes, to obtain the supernatant as the soluble fraction and the precipitate as the insoluble fraction.

The insoluble fraction was suspended in 50 mM Tris-HCl buffer (pH 8.0) and then centrifuged at 6000 rpm for 15 minutes. This operation was repeated twice for removal of proteases.

The residue was suspended in 50 mM Tris-HCl buffer (pH 8.0) supplemented with 6 M guanidine hydrochloride and 0.15 M sodium chloride, and left to stand at 4° C. for 20 hours to denature protein. Thereafter, the suspension was centrifuged at 6000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 50 mM Tris-HCl buffer (pH 8.0) supplemented with 6M guanidine hydrochloride and 0.15 M sodium chloride), followed by leaving the resultant to stand at 4° C. overnight to allow adsorption to the nickel-chelated carrier. The column carrier was centrifuged at 1500 rpm for 5 minutes and the resulting supernatant was recovered. The column carrier was then suspended in phosphate-buffered saline and refilled into the column.

The fraction not adsorbed to the column was washed with 10 column volumes of 0.1 M acetate buffer (pH 4.0) supplemented with 0.5 M sodium chloride, and immediately thereafter, elution with 0.1 M acetate buffer (pH 3.0) supplemented with 0.5 M sodium chloride was carried out to obtain a purified fraction, which was used later as the material for an administration test. The presence of the protein of interest in each eluted fraction was confirmed by Coomassie staining carried out according to a conventional method.

The buffer of the purified preparation obtained by the above method was replaced with a reaction buffer (50 mM Tris-HCl, 100 mM NaCl, 5 mM $CaCl_2$ (pH8.0)), and the resulting sample was subjected to cleavage of the His tag with factor Xa protease and purification of the protein of interest, using Factor Xa Cleavage Capture Kit (manufactured by Novagen) in accordance with the protocol attached to the kit. Subsequently, the buffer of 12 ml of the purified preparation obtained by the above method was replaced with physiological phosphate buffer (manufactured by Nissui Pharmaceutical) using ultrafiltration NANOSEP 10K OMEGA (manufactured by PALL), and the resulting sample was subjected to aseptic filtration through HT Tuffryn Acrodisc 0.22 μm (manufactured by PALL) and used in the experiment.

(3) Induction of CD8-Positive Cytotoxic T Cells Reactive with Human Recombinant SCD1 Protein From a healthy individual, peripheral blood was separated, and the peripheral blood was overlaid on Lymphocyte separation medium (OrganonpTeknika, Durham, N.C.), followed by centrifuging the resultant at 1,500 rpm at room temperature for 20 minutes. A fraction containing peripheral blood mononuclear cells (PBMCs) was recovered and washed 3 (or more) times in cold phosphate buffer, to obtain PBMCs. The obtained PBMCs were suspended in 20 ml of AIM-V medium (Life Technologies, Inc., Grand Island, N.Y., USA), and the cells were allowed to adhere to a culture flask (Falcon) at 37° C. in 5% $CO_2$ for 2 hours. Nonadherent cells were used for preparation of T cells, and adherent cells were used for preparation of dendritic cells.

On the other hand, the adherent cells were cultured in AIM-V medium in the presence of IL-4 (1000 U/ml) and GM-CSF (1000 U/ml). Nonadherent cells obtained 6 days later were collected, and the human recombinant SCD1 protein was added to the cells at a concentration of 10 μg/ml, followed by culturing the cells at 37° C. in 5% $CO_2$ for 4 hours. Thereafter, the medium was replaced with AIM-V medium supplemented with IL-4 (1000 U/ml), GM-CSF (1000 U/ml), IL-6 (1000 U/ml, Genzyme, Cambridge, Mass.), IL-1β (10 ng/ml, Genzyme, Cambridge, Mass.) and TNF-α (10 ng/ml, Genzyme, Cambridge, Mass.), and the culture was carried out for additional 2 days to obtain a population of nonadherent cell to be used as dendritic cells.

The prepared dendritic cells were suspended in AIM-V medium at a cell density of $1 \times 10^6$ cells/ml, and the human recombinant SCD1 protein was added again at a concentration of 10 μg/ml to the suspension. Using a 96-well plate, the cells were cultured at 37° C. in 5% $CO_2$ for 4 hours. After the culture, X-ray irradiation (3000 rads) was carried out, and the cells were washed with AIM-V medium, followed by suspension in AIM-V medium supplemented with 10% human AB serum (Nabi, Miami, Fla.), IL-6 (1000 U/ml) and IL-12 (10 ng/ml, Genzyme, Cambridge, Mass.). The cells were then placed in a 24-well plate in an amount of $1 \times 10^5$ cells/well. Further, the prepared T cell population was added to each well in an amount of $1 \times 10^6$ cells, and cultured at 37° C. in 5% $CO_2$. Each culture supernatant was discarded 7 days later, and dendritic cells obtained in the same manner as described above by treatment with the human SCD1 protein and the subsequent X-ray irradiation were suspended in AIM-V medium supplemented with 10% human AB serum (Nabi, Miami, Fla.), IL-7 (10 U/ml, Genzyme, Cambridge, Mass.) and IL-2 (10 U/ml, Genzyme, Cambridge, Mass.) (cell density, $1 \times 10^5$ cells/ml). The resulting suspension was added to the 24-well plate in an amount of $1 \times 10^5$ cells/well, and the cells were further cultured. After repeating the same operation 4 to 6 times at intervals of 7 days, stimulated T cells were recovered, and induction of CD8-positive T cells was confirmed by flow cytometry.

As a negative control, a protein having a sequence that is outside the scope of the present invention was used (SEQ ID NO:27).

Subsequently, whether or not the CD8-positive T cells stimulated with the present polypeptide can damage SCD1-expressing tumor cells was studied.

In a 50-ml centrifuge tube, $10^5$ cells of a human glioma cell line, U-87MG (purchased from ATCC), in which expression of SCD1 was confirmed, were collected, and 100 μCi chromium 51 was added to the cells, followed by incubation of the resulting mixture at 37° C. for 2 hours. Thereafter, the cells were washed 3 times with AIM-V medium supplemented with 10% human AB serum, and placed in a 96-well V-bottom plate in an amount of $10^3$ cells per well. Subsequently, $10^5$, $5 \times 10^4$, $2.5 \times 10^4$ or $1.25 \times 10^4$ CD8-positive T cells that were stimulated with the human recombinant SCD1 protein and suspended in AIM-V medium supplemented with 10% human AB serum were added to each well, and culture was performed at 37° C. in 5% $CO_2$ for 4 hours. Thereafter, the amount of chromium 51 released from damaged tumor cells in the culture supernatant was measured using a gamma counter to calculate the cytotoxic activity of the CD8-positive T cells stimulated with the human recombinant SCD1 protein.

As a result, it was found that the CD8-positive T cells stimulated with the human recombinant SCD1 protein had cytotoxic activity against U-87MG. On the other hand, the CD8-positive T cells induced using the negative control protein (SEQ ID NO:27) did not show cytotoxic activity. Thus, it was revealed that the human recombinant SCD1 protein used in the present invention has a capacity to induce CD8-positive cytotoxic T cells that can damage tumor cells.

The cytotoxic activity means the cytotoxic activity of the CD8-positive T cells against T98G determined by: mixing $10^5$ CD8-positive T cells stimulated and induced as described above, with $10^3$ cells of the malignant brain tumor cell line U-87MG into which chromium 51 was incorporated; culturing the resulting mixture for 4 hours; measuring the amount of chromium 51 released to the medium after the culture; and then performing calculation according to Equation 1.

Equation 1: Cytotoxic activity (%)=amount of chromium 51 released from U-87MG after addition of CD8-positive T cells (cpm)/amount of chromium 51 released from target cells after addition of 1 N hydrochloric acid (cpm)×100.

INDUSTRIAL APPLICABILITY

The present invention is useful for therapy and/or prophylaxis of cancer since the present invention provides an immunity-inducing agent containing a polypeptide that exerts antitumor activity against various cancers.

The invention claimed is:

1. A method for inducing immunity for therapy of a cancer(s), said method comprising:
    administering to an individual with cancer at least one polypeptide selected from the polypeptides (a) below, and/or a recombinant vector(s) that comprise(s) a polynucleotide(s) encoding said at least one polypeptide, said recombinant vector(s) being capable of expressing said polypeptide(s) in vivo:
    (a) a polypeptide selected from the group consisting of amino acid sequences of SEQ ID NOs: 2, 4, 22, and 24;
    wherein said cancer(s) is/are a cancer(s) expressing SCD1 and wherein said cancer(s) is/are breast cancer, brain tumor, liver cancer, neuroblastoma and/or colon cancer.

2. A method for inducing cytotoxic T cell(s) for therapy of a cancer(s), said method comprising:
    administering to an individual with cancer at least one polypeptide selected from the polypeptides (a) below, and/or a recombinant vector(s) that comprise(s) a polynucleotide(s) encoding said at least one polypeptide, said recombinant vector(s) being capable of expressing said polypeptide(s) in vivo:
    (a) a polypeptide selected from the group consisting of amino acid sequences of SEQ ID NOs: 2, 4, 22, and 24;
    wherein said cancer(s) is/are a cancer(s) expressing SCD1 and wherein said cancer(s) is/are breast cancer, brain tumor, liver cancer, neuroblastoma and/or colon cancer.

3. The method according to claim 2, further comprising administering an immunoenhancer.

4. The method according to claim 3, wherein said immunoenhancer is at least one selected from the group consisting of Freund's incomplete adjuvant, Montanide, poly-I:C, CpG oligonucleotides, interleukin-12, interleukin-18, interferon-α, interferon-β, interferon-ω, interferon-γ, and Flt3 ligand.

5. The method according to claim 2, said method comprising:
    administering to an individual with cancer (i) and (ii) and/or (iii) below:
    (i) the polypeptide;
    (ii) a cytotoxic T cell that selectively binds a complex comprising at least one said polypeptide incorporated into an MHC molecule; and/or
    (iii) an antigen-presenting cell which presents on its surface a complex comprising at least one said polypeptide incorporated into a MHC molecule.

6. The method according to claim 1, further comprising administering an immunoenhancer.

7. The method according to claim 6, wherein said immunoenhancer is at least one selected from the group consisting of Freund's incomplete adjuvant, Montanide, poly-I:C, CpG oligonucleotides, interleukin-12, interleukin-18, interferon-α, interferon-β, interferon-ω, interferon-γ, and Flt3 ligand.

8. The method according to claim 1, said method comprising:
    administering to an individual with cancer (i) and (ii) and/or (iii) below:
    (i) the polypeptide;
    (ii) a cytotoxic T cell that selectively binds a complex comprising at least one said polypeptide incorporated into an MHC molecule; and/or
    (iii) an antigen-presenting cell which presents on its surface a complex comprising at least one said polypeptide incorporated into a MHC molecule.

* * * * *

SEQUENCE LISTING

```
<160> NUMBER OF SEQ ID NOS: 27

<210> SEQ ID NO 1
<211> LENGTH: 5114
<212> TYPE: DNA
<213> ORGANISM: Canis familiaris
<220> FEATURE:
<221> NAME/KEY: CDS
<222> LOCATION: (164)..(1246)
<223> OTHER INFORMATION:

<400> SEQUENCE: 1
ccgagccggc acgcgcggcg cagggaaggt tccgagagcg gcgccgcggg tcaccgcgca      60
gaagcgggct cgggaaccga agtctactcc gcgggcgggc tgtcccggac tccgctgtgc     120
agtctcagcc gcgggaaggt gatccccgcc tcggagagcc cag atg ccg gcc cac      175
                                                 Met Pro Ala His
                                                  1 ttg ctg cag gag gag atc tct agc tcc tac aca acc acc acc atc          223
Leu Leu Gln Glu Glu Ile Ser Ser Ser Tyr Thr Thr Thr Thr Ile
 5                  10                  15                  20 aca gcg cct ccc tcc agg atc ctg cag aat gga gga ggc aag ttg gag      271
Thr Ala Pro Pro Ser Arg Ile Leu Gln Asn Gly Gly Gly Lys Leu Glu
             25                  30                  35 aag cct tcc cta tac ttg gaa gaa gac atc cgc cct gaa atc aaa gat      319
Lys Pro Ser Leu Tyr Leu Glu Glu Asp Ile Arg Pro Glu Ile Lys Asp
         40                  45                  50 gac atc tac gac cca acc tac aag gat ccg gag ggc aga cca aag ccc      367
Asp Ile Tyr Asp Pro Thr Tyr Lys Asp Pro Glu Gly Arg Pro Lys Pro
     55                  60                  65 aag gtt gag tat gtc tgg aga aac atc atc ctt atg tct ctg ctg cac      415
Lys Val Glu Tyr Val Trp Arg Asn Ile Ile Leu Met Ser Leu Leu His
 70                  75                  80 gtg gga gcc ctg tat ggg atc aca ctg att ccc acc tgc aag acg tac      463
Val Gly Ala Leu Tyr Gly Ile Thr Leu Ile Pro Thr Cys Lys Thr Tyr
 85                  90                  95                 100 acc tgg ctc tgg gtg ttc tcc tac tat ctg atc agc gct gtg ggc atc      511
Thr Trp Leu Trp Val Phe Ser Tyr Tyr Leu Ile Ser Ala Val Gly Ile
                 105                 110                 115 aca gca ggg gct cat cgg ctg tgg agt cac cgc acc tac aaa gct cgg      559
Thr Ala Gly Ala His Arg Leu Trp Ser His Arg Thr Tyr Lys Ala Arg
```

-continued

```
                120                 125                 130
ctg ccc ctg agg ctt ttc ctg atc att gcc aac acg atg gca ttc cag    607
Leu Pro Leu Arg Leu Phe Leu Ile Ile Ala Asn Thr Met Ala Phe Gln
        135                 140                 145 aat gac gtg tat gaa tgg gcc cga gat cac cgt gcc cac cac aag ttt    655
Asn Asp Val Tyr Glu Trp Ala Arg Asp His Arg Ala His His Lys Phe
150                 155                 160 tca gaa aca gat gct gat cct cac aat tcc cgg cgt ggc ttt ttc ttc    703
Ser Glu Thr Asp Ala Asp Pro His Asn Ser Arg Arg Gly Phe Phe Phe
165                 170                 175                 180 tct cac gtg ggt tgg ctg ctt gta cgc aaa cac cca gcc gtc aaa gag    751
Ser His Val Gly Trp Leu Leu Val Arg Lys His Pro Ala Val Lys Glu
                185                 190                 195 aag ggt ggt ttg cta gac ttg tct gac cta aaa gct gag aag ctg gtg    799
Lys Gly Gly Leu Leu Asp Leu Ser Asp Leu Lys Ala Glu Lys Leu Val
        200                 205                 210 atg ttc cag aga agg tac tac aaa cct ggc atc ctg ttg atg tgc ttc    847
Met Phe Gln Arg Arg Tyr Tyr Lys Pro Gly Ile Leu Leu Met Cys Phe
        215                 220                 225 atc ctg ccc acc ttt gtg ccc tgg tat ttc tgg ggt gaa act ttt cta    895
Ile Leu Pro Thr Phe Val Pro Trp Tyr Phe Trp Gly Glu Thr Phe Leu
230                 235                 240 cac agt gtg tgc gtt gct act ctc ctg cgt tac gcc att gtg ctc aat    943
His Ser Val Cys Val Ala Thr Leu Leu Arg Tyr Ala Ile Val Leu Asn
245                 250                 255                 260 gcc aca tgg ctg gtg aac agt gct gcc cac ctc tac gga tat cgc cct    991
Ala Thr Trp Leu Val Asn Ser Ala Ala His Leu Tyr Gly Tyr Arg Pro
                265                 270                 275 tac gac aag aat att agc ccc cga gag aat atc ctg gtt tcc ctg gga    1039
Tyr Asp Lys Asn Ile Ser Pro Arg Glu Asn Ile Leu Val Ser Leu Gly
        280                 285                 290 gct gca ggg gag ggc ttc cac aac tac cac cac tcc ttt ccc tat gac    1087
Ala Ala Gly Glu Gly Phe His Asn Tyr His His Ser Phe Pro Tyr Asp
        295                 300                 305 tac tct gcc agt gag tac cgc tgg cac atc aac ttc acc acc ttc ttt    1135
Tyr Ser Ala Ser Glu Tyr Arg Trp His Ile Asn Phe Thr Thr Phe Phe
310                 315                 320 atc gat tgc atg gct gcc ctc ggt ctg gct tac gac cgg aag aaa gta    1183
Ile Asp Cys Met Ala Ala Leu Gly Leu Ala Tyr Asp Arg Lys Lys Val
325                 330                 335                 340 tcc aag gct gcc atc ttg gcc agg att aaa aga act gga gac gga agc    1231
Ser Lys Ala Ala Ile Leu Ala Arg Ile Lys Arg Thr Gly Asp Gly Ser
                345                 350                 355 tac aag agt ggc tga gttttgggtc ccttgggttc cttttccaaa agccagccag    1286
Tyr Lys Ser Gly
            360 gcagaagttt aatgttctgt ttattaacta ctgaataatg ctaccaggat gctaaagatg    1346 atgatgttaa cccattccag tacagtattc ttttaaaatt gaaagccaac aattctgcct    1406 tcatgatgct aagctgatat tcttatttct tctcttatct tctctctctc ctagtccatt    1466 gtccttttct ttgctttgtt cttatcacct tcctttctct cctcgctcat tgcctcccag    1526 gcaaacagct ggtcattcag tgtgggtgt ccagcttcca aagcctagac aaccttttct    1586 ataatccaaa attaatggtc tttgtcccac ataactcttt ccttgagctg tcctgagctt    1646 tagggtgggt ggctcatgct agaggtatga taaaatcttc tgggaaggcc cctgttaatg    1706 atcttcaact caggcttttg tgagttggag tggaaaataa cttatttgg cacaaagctt    1766 ctaaagcagg taaactgtca ggggagagag cgtgcatggt atgattgaga agtaaagatg    1826
```

```
gggtgagatg ggaaacaagg cagaagttca ggctgtgatt ggacacacag ttggtgccta   1886
gtgaggacct caagccccat cagacagcat gcctcctttc tctcctgact ctgactaggg   1946
aatggccata gagcctggca atgctagatt acaaaagcaa atctcaatgt cccaatgtag   2006
tttaggttgg ggataaagaa gaagcattta gtttgtagtc aaagtggtct ttgctgggga   2066 aggattttt ttttttaaa taacaggaag atttcttatt ccatattaca agaaatcttg    2126
aggttggttg tttccagaat tggtgaatct agcagatcat ggaatcatca aaattctttc   2186
atctttctgc tctgccatct tcgggacatt ggtcagctcc atcatagtaa taacgtggct   2246
gaagcatttc cagacatcca aaaaggaac atgtttgtgg catagtggtg agcatggctg    2306
tcttccaaaa aaggaaggat tttaagaagt ggagttgggt ccgacataaa aataatatac   2366
attcactctg cttggaacat taagtaatt cacttagggt atttccctct ggagaagagg    2426
agaaattagg tgggttgtct actttcctct cactgctgga caggagatgg agagttcagg   2486
ggcagggtct gttggcaatt cctaagagaa aactttataa agaagggct ctgagaacac    2546 attgccagag gattcagagg gttactaaga aagtcaatgg gtgtcctgat ttggaagctg   2606
gttatacaag caagtaaatg ttcagttcat tcattaattc catttctcct tgggatgagt   2666
aaaaactaga aggcttctcc ccgcagtgct gaaccatttc tcccattcct tctctgctaa   2726
cttttcacct aaagtatagg actgcctggg gcggggggcga ggtaggaatc taactactgt   2786 ggttttgat tcctggctct acccttttccg tccatttct cctaccggtt ctatctcctt    2846
cctccctgat gtgttcttct ctctctggac aggaagcctg ctttgtatgt attccgaggc   2906
agtgatgatt attgcccacc gggcagctcc ctctcctgca gacagaatgc tcagggtcac   2966
tgaaccactg tttctcttta taaagttgag ttagctgcca ctttcacttg gcctccagag   3026
tctctccacc tacacccctg tgcgccctg ccacactgat gactcaagat gaggctggca    3086
aacgttacta gaaacatccc tggctcaggc actctctctc tcaggaggca cagccaggcc   3146
acatgctcgt gttgtgccag tgagccagcc acggagcaaa aaacggtttg ttttttaacct  3206 cctctgtctg gatcacaaca tgagagtatg ctagatgccc cctgcttgct cagtaagcct   3266
gcccagccct agtccgtgct cccagcggac agtgcaatgc ttgtagaagt aggagggagc   3326
ctagtcttca ctgggaagca caagaagcaa aggaaagtcc caaagtgcct catgcaaaag   3386
gaggccctgt tccctggagc cagggtgtat tacgaagccg agacttggga tctgagatgc   3446
catgaacttt gctgaacagc atctctgttt ggcaaactaa ccagcattcc ccaccaccca   3506
gcctagggca aatggtagtg tagaagaggt ctgaaaaaaa gcaccagtgt tttgagaacc   3566
ttggactact catgtccctg tacctcagtc atcaatgcaa aggcctggct ttactctatg   3626
aaagattgga aatctacaat accaaatgtc ctgtgcattg ttgaggaata gtggaaagaa   3686
agaaggcctt tcttcctgta ttaattgaat agacagaggc tacaggggtt ccctggacta   3746
aaggcatcct tgtctttga gctgttcctc tcagtagaaa caaatctaat ggaagatcac    3806
ggcgtagtgt agatctgctg acttgtgtac ctatctcttg gagatccctg ttgggtagtt   3866
ttaattccac aggttagcag atgcctgctt tctaattttg gaccaaaaac aagcttatct   3926
ttctattcta atcacgtccc agggatctga cccataccat gacccttcac aagactggac   3986
aagggcctca ggctgagggc tcctatgact atgacaatgt ggaggtggag gggtgtctac   4046
tgagtaagga acacttattt caagattcta aagctgagtt caattgacac attaatgatc   4106
cagaaactca agtctgaatt tctaacagtc ctcacttcgt gggtatgctg acaacttatt   4166
```

```
tgggtgcctt acatctgttc taatcagtgt tgtatatgag cctacttccg ctccctcctc    4226
gctcccctg tggagttcct ttgcacctgc gaccctacag aagtggttgg tagaaaaggg    4286
ggcctggctg gagaattatc agtatagcta ttcacaagat ttccttctgg ctttttttt    4346
tagggctgtt tttcttaagt gcccacattt gatggagggt ggaagtaatt tgaatgtatt    4406
tgatttataa ttcttttag gttaaaagat ggtgtagcat ttaaaatgga aactttctct    4466
ccttggtttg ctagtatcct gagtgtattc tctgtaagta tagctcaaat gggtcagtgt    4526
gaaaggttaa caaaagcaag atgtcaatgt tacgtgggtg gttaaggcca gggcctcccc    4586
taccactgtg ccactgactt gctgtgtgac cctgggcaag tcacttaact ataatgtgcc    4646
tcagttttcc ttctgttaaa atgggataat aatactgacc tacctcaaag ggcagttttg    4706
aggcgtgact aatgcttttt ataaagcatt ttgggatcct tcagcagagg aattcttta    4766
agtcctgagt attttatag tagcagtatc caccgtgaac ttatgtccac cgtaaaccac    4826
gtgtcctatc attaatcgat attctctctg agagattgga taaatccatt ggataagtgg    4886
tggataacta gccagacaaa atttgagaat gcataaactc attgccatgg aaacaataca    4946
caggatacct tttccttaat tgggtgggat ttttccctt ttatgtggga tagtagttat    5006
ttgtgaccta agaataattt tggaataatt tctattaata tcaactctga agcttagttg    5066
tactgatctg aaattgtgtt tgttcataat aaaagtgaag tgaatctg              5114
```

<210> SEQ ID NO 2
<211> LENGTH: 360
<212> TYPE: PRT
<213> ORGANISM: Canis familiaris

<400> SEQUENCE: 2

```
Met Pro Ala His Leu Leu Gln Glu Glu Ile Ser Ser Tyr Thr Thr
1               5                   10                  15

Thr Thr Thr Ile Thr Ala Pro Pro Ser Arg Ile Leu Gln Asn Gly Gly
            20                  25                  30

Gly Lys Leu Glu Lys Pro Ser Leu Tyr Leu Glu Glu Asp Ile Arg Pro
        35                  40                  45

Glu Ile Lys Asp Asp Ile Tyr Asp Pro Thr Tyr Lys Asp Pro Glu Gly
    50                  55                  60

Arg Pro Lys Pro Lys Val Glu Tyr Val Trp Arg Asn Ile Ile Leu Met
65                  70                  75                  80

Ser Leu Leu His Val Gly Ala Leu Tyr Gly Ile Thr Leu Ile Pro Thr
                85                  90                  95

Cys Lys Thr Tyr Thr Trp Leu Trp Val Phe Ser Tyr Tyr Leu Ile Ser
            100                 105                 110

Ala Val Gly Ile Thr Ala Gly Ala His Arg Leu Trp Ser His Arg Thr
        115                 120                 125

Tyr Lys Ala Arg Leu Pro Leu Arg Leu Phe Leu Ile Ile Ala Asn Thr
    130                 135                 140

Met Ala Phe Gln Asn Asp Val Tyr Glu Trp Ala Arg Asp His Arg Ala
145                 150                 155                 160

His His Lys Phe Ser Glu Thr Asp Ala Asp Pro His Asn Ser Arg Arg
                165                 170                 175

Gly Phe Phe Phe Ser His Val Gly Trp Leu Leu Val Arg Lys His Pro
            180                 185                 190

Ala Val Lys Glu Lys Gly Gly Leu Leu Asp Leu Ser Asp Leu Lys Ala
        195                 200                 205
```

```
Glu Lys Leu Val Met Phe Gln Arg Arg Tyr Tyr Lys Pro Gly Ile Leu
    210                 215                 220
Leu Met Cys Phe Ile Leu Pro Thr Phe Val Pro Trp Tyr Phe Trp Gly
225                 230                 235                 240
Glu Thr Phe Leu His Ser Val Cys Val Ala Thr Leu Leu Arg Tyr Ala
                245                 250                 255
Ile Val Leu Asn Ala Thr Trp Leu Val Asn Ser Ala Ala His Leu Tyr
            260                 265                 270
Gly Tyr Arg Pro Tyr Asp Lys Asn Ile Ser Pro Arg Glu Asn Ile Leu
        275                 280                 285
Val Ser Leu Gly Ala Ala Gly Glu Gly Phe His Asn Tyr His His Ser
    290                 295                 300
Phe Pro Tyr Asp Tyr Ser Ala Ser Glu Tyr Arg Trp His Ile Asn Phe
305                 310                 315                 320
Thr Thr Phe Phe Ile Asp Cys Met Ala Ala Leu Gly Leu Ala Tyr Asp
                325                 330                 335
Arg Lys Lys Val Ser Lys Ala Ala Ile Leu Ala Arg Ile Lys Arg Thr
            340                 345                 350
Gly Asp Gly Ser Tyr Lys Ser Gly
        355                 360

<210> SEQ ID NO 3
<211> LENGTH: 5473
<212> TYPE: DNA
<213> ORGANISM: Homo sapiens
<220> FEATURE:
<221> NAME/KEY: CDS
<222> LOCATION: (491)..(1570)
<223> OTHER INFORMATION:

<400> SEQUENCE: 3
ggcaggacga ggtggcacca aattcccttc ggccaatgac gagccggagt ttacagaagc    60
ctcattagca tttccccaga ggcaggggca ggggcagagg ccgggtggtg tggtgtcggt   120
gtcggcagca tccccggcgc cctgctgcgg tcgccgcgag cctcggcctc tgtctcctcc   180
ccctcccgcc cttacctcca cgcgggaccc ccgcgccag tcaactcctc gcactttgcc   240
cctgcttggc agcggataaa aggggggctga ggaaataccg acacggtca cccgttgcca   300 gctctagcct ttaaattccc ggctcgggga cctccacgca ccgcggctag cgccgacaac   360
cagctagcgt gcaaggcgcc gcggctcagc gcgtaccggc gggcttcgaa accgcagtcc   420
tccggcgacc ccgaactccg ctccggagcc tcagcccccct ggaaagtgat cccggcatcc   480
gagagccaag atg ccg gcc cac ttg ctg cag gac gat atc tct agc tcc   529
           Met Pro Ala His Leu Leu Gln Asp Asp Ile Ser Ser Ser
               1               5                   10 tat acc acc acc acc acc att aca gcg cct ccc tcc agg gtc ctg cag   577
Tyr Thr Thr Thr Thr Thr Ile Thr Ala Pro Pro Ser Arg Val Leu Gln
    15                  20                  25 aat gga gga gat aag ttg gag acg atg ccc ctc tac ttg gaa gac gac   625
Asn Gly Gly Asp Lys Leu Glu Thr Met Pro Leu Tyr Leu Glu Asp Asp
30                  35                  40                  45 att cgc cct gat ata aaa gat gat ata tat gac ccc acc tac aag gat   673
Ile Arg Pro Asp Ile Lys Asp Asp Ile Tyr Asp Pro Thr Tyr Lys Asp
                50                  55                  60 aag gaa ggc cca agc ccc aag gtt gaa tat gtc tgg aga aac atc atc   721
Lys Glu Gly Pro Ser Pro Lys Val Glu Tyr Val Trp Arg Asn Ile Ile
            65                  70                  75 ctt atg tct ctg cta cac ttg gga gcc ctg tat ggg atc act ttg att   769
```

-continued

```
              Leu Met Ser Leu Leu His Leu Gly Ala Leu Tyr Gly Ile Thr Leu Ile
                       80                  85                  90 cct acc tgc aag ttc tac acc tgg ctt tgg ggg gta ttc tac tat ttt          817
Pro Thr Cys Lys Phe Tyr Thr Trp Leu Trp Gly Val Phe Tyr Tyr Phe
         95                 100                 105 gtc agt gcc ctg ggc ata aca gca gga gct cat cgt ctg tgg agc cac          865
Val Ser Ala Leu Gly Ile Thr Ala Gly Ala His Arg Leu Trp Ser His
110                 115                 120                 125 cgc tct tac aaa gct cgg ctg ccc cta cgg ctc ttt ctg atc att gcc          913
Arg Ser Tyr Lys Ala Arg Leu Pro Leu Arg Leu Phe Leu Ile Ile Ala
                 130                 135                 140 aac aca atg gca ttc cag aat gat gtc tat gaa tgg gct cgt gac cac          961
Asn Thr Met Ala Phe Gln Asn Asp Val Tyr Glu Trp Ala Arg Asp His
             145                 150                 155 cgt gcc cac cac aag ttt tca gaa aca cat gct gat cct cat aat tcc         1009
Arg Ala His His Lys Phe Ser Glu Thr His Ala Asp Pro His Asn Ser
         160                 165                 170 cga cgt ggc ttt ttc ttc tct cac gtg ggt tgg ctg ctt gtg cgc aaa         1057
Arg Arg Gly Phe Phe Phe Ser His Val Gly Trp Leu Leu Val Arg Lys
     175                 180                 185 cac cca gct gtc aaa gag aag ggg agt acg cta gac ttg tct gac cta         1105
His Pro Ala Val Lys Glu Lys Gly Ser Thr Leu Asp Leu Ser Asp Leu
190                 195                 200                 205 gaa gct gag aaa ctg gtg atg ttc cag agg agg tac tac aaa cct ggc         1153
Glu Ala Glu Lys Leu Val Met Phe Gln Arg Arg Tyr Tyr Lys Pro Gly
                 210                 215                 220 ttg ctg atg atg tgc ttc atc ctg ccc acg ctt gtg ccc tgg tat ttc         1201
Leu Leu Met Met Cys Phe Ile Leu Pro Thr Leu Val Pro Trp Tyr Phe
             225                 230                 235 tgg ggt gaa act ttt caa aac agt gtg ttc gtt gcc act ttc ttg cga         1249
Trp Gly Glu Thr Phe Gln Asn Ser Val Phe Val Ala Thr Phe Leu Arg
         240                 245                 250 tat gct gtg gtg ctt aat gcc acc tgg ctg gtg aac agt gct gcc cac         1297
Tyr Ala Val Val Leu Asn Ala Thr Trp Leu Val Asn Ser Ala Ala His
     255                 260                 265 ctc ttc gga tat cgt cct tat gac aag aac att agc ccc cgg gag aat         1345
Leu Phe Gly Tyr Arg Pro Tyr Asp Lys Asn Ile Ser Pro Arg Glu Asn
270                 275                 280                 285 atc ctg gtt tca ctt gga gct gtg ggt gag ggc ttc cac aac tac cac         1393
Ile Leu Val Ser Leu Gly Ala Val Gly Glu Gly Phe His Asn Tyr His
                 290                 295                 300 cac tcc ttt ccc tat gac tac tct gcc agt gag tac cgc tgg cac atc         1441
His Ser Phe Pro Tyr Asp Tyr Ser Ala Ser Glu Tyr Arg Trp His Ile
             305                 310                 315 aac ttc acc aca ttc ttc att gat tgc atg gcc gcc ctc ggt ctg gcc         1489
Asn Phe Thr Thr Phe Phe Ile Asp Cys Met Ala Ala Leu Gly Leu Ala
         320                 325                 330 tat gac cgg aag aaa gtc tcc aag gcc gcc atc ttg gcc agg att aaa         1537
Tyr Asp Arg Lys Lys Val Ser Lys Ala Ala Ile Leu Ala Arg Ile Lys
     335                 340                 345 aga acc gga gat gga aac tac aag agt ggc tga gtttggggtc cctcaggttc       1590
Arg Thr Gly Asp Gly Asn Tyr Lys Ser Gly
350                 355 cttttttcaaa aaccagccag gcagaggttt taatgtctgt ttattaacta ctgaataatg      1650
ctaccaggat gctaaagatg atgatgttaa cccattccag tacagtattc ttttaaaatt      1710
caaaagtatt gaaagccaac aactctgcct ttatgatgct aagctgatat tatttcttct      1770
cttatcctct ctctcttcta ggcccattgt cctcctttttc actttattgc tatcgccctc    1830
```

```
ctttccctta ttgcctccca ggcaagcagc tggtcagtct ttgctcagtg tccagcttcc      1890
aaagcctaga caacctttct gtagcctaaa acgaatggtc tttgctccag ataactctct      1950
ttccttgagc tgttgtgagc tttgaagtag gtggcttgag ctagagataa aacagaatct      2010
tctgggtagt cccctgttga ttatcttcag cccaggcttt tgctagatgg aatggaaaag      2070
caacttcatt tgacacaaag cttctaaagc aggtaaattg tcgggggaga gagttagcat      2130
gtatgaatgt aaggatgagg gaagcgaagc aagaggaacc tctcgccatg atcagacata      2190
cagctgccta cctaatgagg acttcaagcc ccaccacata gcatgcttcc tttctctcct      2250
ggctcggggt aaaaagtggc tgcggtgttt ggcaatgcta attcaatgcc gcaacatata      2310
gttgaggccg aggataaaga aaagacattt taagtttgta gtaaaagtgg tctctgctgg      2370
ggaagggttt tcttttcttt ttttctttaa taacaaggag atttcttagt tcatatatca      2430
agaagtcttg aagttgggtg tttccagaat tggtaaaaac agcagctcat agaattttga      2490
gtattccatg agctgctcat tacagttctt cctctttct gctctgccat cttcaggata       2550
ttggttcttc ccctcatagt aataagatgg ctgtggcatt tccaaacatc caaaaaagg       2610
gaaggattta aggaggtgaa gtcgggtcaa aaataaaata tatatacata tatacattgc      2670
ttagaacgtt aaactattag agtatttccc ttccaaagag ggatgtttgg aaaaaactct      2730
gaaggagagg aggaattagt tgggatgcca atttcctctc cactgctgga catgagatgg      2790
agaggctgag ggacaggatc tataggcagc ttctaagagc gaacttcaca taggaaggga      2850
tctgagaaca cgttgccagg ggcttgagaa ggttactgag tgagttattg ggagtcttaa      2910
taaaataaac tagatattag gtccattcat taattagttc cagtttctcc ttgaaatgag      2970
taaaaactag aaggcttctc tccacagtgt tgtgcccctt cactcatttt tttttgagga     3030
gaaggggtc tctgttaaca tctagcctaa agtatacaac tgcctgggg gcagggttag       3090
gaatctcttc actaccctga ttcttgattc ctggctctac cctgtctgtc ccttttcttt     3150
gaccagatct ttctcttccc tgaacgtttt cttctttccc tggacaggca gcctcctttg     3210
tgtgtattca gaggcagtga tgacttgctg tccaggcagc tccctcctgc acacagaatg     3270
ctcagggtca ctgaaccact gcttctcttt tgaaagtaga gctagctgcc actttcacgt     3330
ggcctccgca gtgtctccac ctacacccct gtgctcccct gccacactga tggctcaaga    3390
caaggctggc aaaccctccc agaaacatct ctggcccaga aagcctctct ctccctccct    3450
ctctcatgag gcacagccaa gccaagcgct catgttgagc cagtgggcca gccacagagc   3510
aaaagagggt ttatttcag tccctctct ctgggtcaga accagagggc atgctgaatg      3570
ccccctgctt acttggtgag ggtgccccgc ctgagtcagt gctctcagct ggcagtgcaa   3630
tgcttgtaga agtaggagga aacagttctc actgggaaga agcaagggca agaacccaag   3690
tgcctcacct cgaaggagg ccctgttccc tggagtcagg gtgaactgca aagctttggc    3750
tgagacctgg gatttgagat accacaaacc ctgctgaaca cagtgtctgt tcagcaaact   3810
aaccagcatt ccctacagcc tagggcagac aatagtatag aagtctggaa aaaaacaaaa   3870
acagaatttg agaaccttgg accactcctg tccctgtagc tcagtcatca agcagaagt    3930
ctggctttgc tctattaaga ttggaaatgt acactaccaa acactcagtc cactgttgag   3990
ccccagtgct ggaagggagg aaggcctttc ttctgtgtta attgcgtaga ggctacaggg   4050
gttagcctgg actaaaggca tccttgtctt ttgagctatt cacctcagta gaaaaggatc   4110
taagggaaga tcactgtagt ttagttctgt tgacctgtgc acctacccct tggaaatgtc   4170
tgctggtatt tctaattcca caggtcatca gatgcctgct tgataatata taaacaataa   4230
```

```
aaacaacttt cacttcttcc tattgtaatc gtgtgccatg gatctgatct gtaccatgac    4290
cctacataag gctggatggc acctcaggct gagggcccca atgtatgtgt ggctgtgggt    4350
gtgggtggga gtgtgtctgc tgagtaagga acacgatttt caagattcta agctcaatt    4410
caagtgacac attaatgata aactcagatc tgatcaagag tccggatttc taacagtcct    4470
tgctttgggg ggtgtgctga caacttagct caggtgcctt acatcttttc taatcacagt    4530
gttgcatatg agcctgccct cactccctct gcagaatccc tttgcacctg agaccctact    4590
gaagtggctg gtagaaaaag gggcctgagt ggaggattat cagtatcacg atttgcagga    4650
ttcccttctg ggcttcattc tggaaacttt tgttagggct gcttttctta agtgcccaca    4710
tttgatggag ggtggaaata atttgaatgt atttgattta aagtttttt ttttttttt     4770
ggggttaaaag atggttgtag catttaaaat ggaaatttt ctccttggtt tgctagtatc    4830
ttgggtgtat tctctgtaag tgtagctcaa ataggtcatc atgaaaggtt aaaaaagcga    4890
ggtggccatg ttatgctggt ggttaaggcc agggcctctc caaccactgt gccactgact    4950
tgctgtgtga ccctgggcaa gtcacttaac tataaggtgc ctcagttttc cttctgttaa    5010
aatggggata taatactga cctacctcaa agggcagttt tgaggcatga ctaatgcttt     5070
ttagaaagca ttttgggatc cttcagcaca ggaattctca agacctgagt attttttata    5130
ataggaatgt ccaccatgaa cttgatacgt ccgtgtgtcc cagatgctgt cattagtcta    5190
tatggttctc caagaaactg aatgaatcca ttggagaagc ggtggataac tagccagaca    5250
aaatttgaga atacataaac aacgcattgc cacggaaaca tacagaggat gccttttctg    5310
tgattgggtg ggatttttc ccttttatg tgggatatag tagttacttg tgacaagaat      5370
aattttggaa taatttctat taatatcaac tctgaagcta attgtactaa tctgagattg    5430
tgtttgttca taataaaagt gaagtgaatc tgattgcaaa aaa                      5473
```

<210> SEQ ID NO 4
<211> LENGTH: 359
<212> TYPE: PRT
<213> ORGANISM: Homo sapiens

<400> SEQUENCE: 4

Met Pro Ala His Leu Leu Gln Asp Asp Ile Ser Ser Tyr Thr Thr
1               5                   10                  15

Thr Thr Thr Ile Thr Ala Pro Pro Ser Arg Val Leu Gln Asn Gly Gly
                20                  25                  30

Asp Lys Leu Glu Thr Met Pro Leu Tyr Leu Glu Asp Asp Ile Arg Pro
            35                  40                  45

Asp Ile Lys Asp Asp Ile Tyr Asp Pro Thr Tyr Lys Asp Lys Glu Gly
        50                  55                  60

Pro Ser Pro Lys Val Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Phe Tyr Thr Trp Leu Trp Gly Val Phe Tyr Phe Val Ser Ala
                100                 105                 110

Leu Gly Ile Thr Ala Gly Ala His Arg Leu Trp Ser His Arg Ser Tyr
            115                 120                 125

Lys Ala Arg Leu Pro Leu Arg Leu Phe Leu Ile Ile Ala Asn Thr Met
        130                 135                 140

Ala Phe Gln Asn Asp Val Tyr Glu Trp Ala Arg Asp His Arg Ala His

```
                145                 150                 155                 160
        His Lys Phe Ser Glu Thr His Ala Asp Pro His Asn Ser Arg Arg Gly
                        165                 170                 175

Phe Phe Phe Ser His Val Gly Trp Leu Leu Val Arg Lys His Pro Ala
                        180                 185                 190

Val Lys Glu Lys Gly Ser Thr Leu Asp Leu Ser Asp Leu Glu Ala Glu
                        195                 200                 205

Lys Leu Val Met Phe Gln Arg Arg Tyr Tyr Lys Pro Gly Leu Leu Met
                210                 215                 220

Met Cys Phe Ile Leu Pro Thr Leu Val Pro Trp Tyr Phe Trp Gly Glu
        225                 230                 235                 240

Thr Phe Gln Asn Ser Val Phe Val Ala Thr Phe Leu Arg Tyr Ala Val
                        245                 250                 255

Val Leu Asn Ala Thr Trp Leu Val Asn Ser Ala Ala His Leu Phe Gly
                        260                 265                 270

Tyr Arg Pro Tyr Asp Lys Asn Ile Ser Pro Arg Glu Asn Ile Leu Val
                        275                 280                 285

Ser Leu Gly Ala Val Gly Glu Gly Phe His Asn Tyr His His Ser Phe
                290                 295                 300

Pro Tyr Asp Tyr Ser Ala Ser Glu Tyr Arg Trp His Ile Asn Phe Thr
        305                 310                 315                 320

Thr Phe Phe Ile Asp Cys Met Ala Ala Leu Gly Leu Ala Tyr Asp Arg
                        325                 330                 335

Lys Lys Val Ser Lys Ala Ala Ile Leu Ala Arg Ile Lys Arg Thr Gly
                        340                 345                 350

Asp Gly Asn Tyr Lys Ser Gly
                355

<210> SEQ ID NO 5
<211> LENGTH: 4844
<212> TYPE: DNA
<213> ORGANISM: Mus musculus
<220> FEATURE:
<221> NAME/KEY: CDS
<222> LOCATION: (301)..(1368)
<223> OTHER INFORMATION:

<400> SEQUENCE: 5
cacctccacg cctggcttcc ttggctagct atctctgcgc tctttaccct ttgctggcag      60
ccgataaaag ggggctgagg aaatactgaa cacggtcatc ccatcgcctg ctctacccct     120
taaaatccca gcccagggag atctgtgcac agccagaccg ggctgaacac ccatcccgag     180
agtcaggagg gcaggtttcc aagcgcagtt ccgccactcg cctacaccaa cgggctccgg     240
aaccgaagtc cacgctcgat ctcagcactg ggaaagtgag gcgagcaact gactatcatc     300 atg ccg gcc cac atg ctc caa gag atc tcc agt tct tac acg acc acc       348
Met Pro Ala His Met Leu Gln Glu Ile Ser Ser Ser Tyr Thr Thr Thr
 1               5                  10                  15 acc acc atc act gca cct ccc tcc gga aat gaa cga gag aag gtg aag       396
Thr Thr Ile Thr Ala Pro Pro Ser Gly Asn Glu Arg Glu Lys Val Lys
                20                  25                  30 acg gtg ccc ctc cac ctg gaa gaa gac atc cgt cct gaa atg aaa gaa       444
Thr Val Pro Leu His Leu Glu Glu Asp Ile Arg Pro Glu Met Lys Glu
            35                  40                  45 gat att cac gac ccc acc tat cag gat gag gag gga ccc ccg ccc aag       492
Asp Ile His Asp Pro Thr Tyr Gln Asp Glu Glu Gly Pro Pro Pro Lys
        50                  55                  60
```

```
ctg gag tac gtc tgg agg aac atc att ctc atg gtc ctg ctg cac ttg      540
Leu Glu Tyr Val Trp Arg Asn Ile Ile Leu Met Val Leu Leu His Leu
 65                  70                  75                  80 gga ggc ctg tac ggg atc ata ctg gtt ccc tcc tgc aag ctc tac acc      588
Gly Gly Leu Tyr Gly Ile Ile Leu Val Pro Ser Cys Lys Leu Tyr Thr
                     85                  90                  95 tgc ctc ttc ggg att ttc tac tac atg acc agc gct ctg ggc atc aca      636
Cys Leu Phe Gly Ile Phe Tyr Tyr Met Thr Ser Ala Leu Gly Ile Thr
                100                 105                 110 gcc ggg gct cat cgc ctc tgg agc cac aga act tac aag gca cgg ctg      684
Ala Gly Ala His Arg Leu Trp Ser His Arg Thr Tyr Lys Ala Arg Leu
            115                 120                 125 ccc ctg cgg atc ttc ctt atc att gcc aac acc atg gcg ttc cag aat      732
Pro Leu Arg Ile Phe Leu Ile Ile Ala Asn Thr Met Ala Phe Gln Asn
        130                 135                 140 gac gtg tac gaa tgg gcc cga gat cac cgc gcc cac cac aag ttc tca      780
Asp Val Tyr Glu Trp Ala Arg Asp His Arg Ala His His Lys Phe Ser
145                 150                 155                 160 gaa aca cac gcc gac cct cac aat tcc cgc cgt ggc ttc ttc ttc tct      828
Glu Thr His Ala Asp Pro His Asn Ser Arg Arg Gly Phe Phe Phe Ser
                    165                 170                 175 cac gtg ggt tgg ctg ctt gtg cgc aaa cac ccg gct gtc aaa gag aag      876
His Val Gly Trp Leu Leu Val Arg Lys His Pro Ala Val Lys Glu Lys
                180                 185                 190 ggc gga aaa ctg gac atg tct gac ctg aaa gcc gag aag ctg gtg atg      924
Gly Gly Lys Leu Asp Met Ser Asp Leu Lys Ala Glu Lys Leu Val Met
            195                 200                 205 ttc cag agg agg tac tac aag ccc ggc ctc ctg atg tgc ttc atc          972
Phe Gln Arg Arg Tyr Tyr Lys Pro Gly Leu Leu Met Cys Phe Ile
        210                 215                 220 ctg ccc acg ctg gtg ccc tgg tac tgc tgg ggc gag act ttt gta aac     1020
Leu Pro Thr Leu Val Pro Trp Tyr Cys Trp Gly Glu Thr Phe Val Asn
225                 230                 235                 240 agc ctg ttc gtt agc acc ttc ttg cga tac act ctg gtg ctc aac gcc     1068
Ser Leu Phe Val Ser Thr Phe Leu Arg Tyr Thr Leu Val Leu Asn Ala
                    245                 250                 255 acc tgg ctg gtg aac agt gcc gcg cat ctc tat gga tat cgc ccc tac     1116
Thr Trp Leu Val Asn Ser Ala Ala His Leu Tyr Gly Tyr Arg Pro Tyr
                260                 265                 270 gac aag aac att caa tcc cgg gag aat atc ctg gtt tcc ctg ggt gcc     1164
Asp Lys Asn Ile Gln Ser Arg Glu Asn Ile Leu Val Ser Leu Gly Ala
            275                 280                 285 gtg ggc gag ggc ttc cac aac tac cac cac acc ttc ccc ttc gac tac     1212
Val Gly Glu Gly Phe His Asn Tyr His His Thr Phe Pro Phe Asp Tyr
        290                 295                 300 tct gcc agt gag tac cgc tgg cac atc aac ttc acc acg ttc ttc atc     1260
Ser Ala Ser Glu Tyr Arg Trp His Ile Asn Phe Thr Thr Phe Phe Ile
305                 310                 315                 320 gac tgc atg gct gcc ctg ggc ctg gct tac gac cgg aag aaa gtt tct     1308
Asp Cys Met Ala Ala Leu Gly Leu Ala Tyr Asp Arg Lys Lys Val Ser
                    325                 330                 335 aag gct act gtc tta gcc agg att aag aga act gga gac ggg agt cac     1356
Lys Ala Thr Val Leu Ala Arg Ile Lys Arg Thr Gly Asp Gly Ser His
                340                 345                 350 aag agt agc tga gctttgggct tctgagttcc tgtttcaaac gttttctggc         1408
Lys Ser Ser
        355 agagatttaa tattctgttg attaactaac aactggatat tgctatcggg gtgttaatga   1468
```

```
tgcatttaac ctattccggt acagtattct tataaaatga gaaagctttg atcacgtttt    1528
gaggtaataa atattttatt tagctaggat taaccatgcc acaagacatt atatatttct    1588
aagcacacat gataaatgca tatacaattt tgcacaacag ctttaaataa taacaataaa    1648
tttgaacatt ctatacagag aggatcaaag ccaaggaaca tgctgttttg atgctagggt    1708
gagcatggtg ctcagtccct gtttgtttgc atggtgtcca gctttgtttc ttctctgtca    1768
tcaccacctt caggcaaata gttgaccaac cactggcctg tgtctgtcca ccctccaaag    1828
cccaggccac ctttctgttt tctgaaatac tgatccttcc tcctgaatac atccctcctt    1888
gttcctagct tcaagactgc tgcctcaaac tagggataga gcaagtcccc gctgatgaag    1948
ttcactgcag gttgtgctag atgggatgga gaaattatct tcatttgata cagagcaagt    2008
agattgtctc gagagaaaag ttagcatgcg tggtatgatt tgtaagtaaa gatggaagag    2068
agagagagag agagagagag agagagagag agagaggtag ccatatctaa cagcctactt    2128
accaaagacc ccaggcctct ctgcttggca tgcctccttt ctgtccatcc tctgaaccec    2188 agagattagt gagatttgaa taattaaatc attttcagag tgaaggggt taatgcaggg     2248 tctgtgctag gggagggttt tagcttttgg taactgaaga ttttttcatg gaaaagtct     2308 tcgtgttcaa tgtgcctaga actgataact aaacagctga catttgtcgg ggacagatat    2368
ggtgtgaaac tatgaaaata taagcaaaat cttcacttgg aacatgaaac tatttcactt    2428 agaaataat cgaaggaccc gaggtgttgc ctggttgcc agtttctttc gtggctgggc      2488
aggaactagt gaggttgagg ggcagtgtct gtaagtagct gctaagaggt gcatttccag    2548
atgaagccct tggggaacat ctgccaggga tccgcatggt gttggctcca tccattgctt    2608
tagtttcctc cttggattgt gtagaaactt ggcttcccat ggttttgaac cttccatgcc    2668
ttctttgctt tgtggccacc cagcctgcct agtgctgcct aggaagctct tacccacctg    2728
atttcttctg acatttcttt ctttggcctt ttttcttc tccggacatg cagctagttg      2788
cctgagtgta tcaagagcac ccaggacttg ctgctgtcca ggcctgttcc tccccagta    2848 tccgtgggtg tggaagagct gtgtagcttc aggaagcaga gccaggtgcc acctttctgt   2908
ggcttccaga tcctccctac ctccaactca tgtgcctctg tcacagtgat ttcaggaaag   2968
cttggtagac cctctagcaa catctcggtt cagaaagtct ctctggtttg tgagttaaca   3028
gctcagctaa gtgctgtttt gtctcagtga gttaaccact gaatgcgagg gttggttgtt   3088
gatctgtctc ggtgtgtgtc ggagtagaca gcatatgcac ttctccctgt gcgctttgca   3148
aggtaatgtg gctttggctg atccatgcag gcaggtagtg gtacagtgct gctgaaagga   3208
agaagttccc cattttatct gttaaaacac cagagacatg ggcaagtgct aatggacctc   3268
acttcaggaa gagggtctgc ttcctgaagc cagtgtgtga tgaaaagtga ctgagacctg   3328
atatctaagg tgagacctga tacctaacac tctgtcacac agtccagggc caacagtgct   3388
ataggaaagt ctagaagaaa acatcacatc agtattttag aaccatcaac catctcttgt   3448
ccctatagcc caatccagag gcctggtttt tagaactggc tgtgtaaggt gccaaacact   3508
cagttcactt gtagaatcag agccttttt ccccctatg ttaattgaac acgcgctctg     3568
agctgttttg ttgaagtaga aaatctcata gaaaatcac tgtagatcta ctgacctata    3628
gccctctgga aatgcctttg agatggtttt acttttctag gtcatagatg cctgatttat   3688
aagatgaaca ataaaatcag ctttcttct ttctcttctg atcttattcc ccagatctga    3748
ttcaggccat gttccaaagc aaggctacat tgaggtcctg gtgtctttaa gtaaaggaca   3808
```

```
tctttcagat cctctcaaag aaggatttat aacagtttcc agatgaatgt actaatagct    3868
ttgggtgcct tatctctttc ctaatctgta gtgcctgtga gctcagtctc actccttccc    3928
ttagcccgga gacccctag atcgagtggg aatagtcaag aggctggctg gagagtcatc    3988
```

```
tctttcagat cctctcaaag aaggatttat aacagtttcc agatgaatgt actaatagct    3868
ttgggtgcct tatctctttc ctaatctgta gtgcctgtga gctcagtctc actccttccc    3928
ttagcccgga gacccttag atcgagtggg aatagtcaag aggctggctg gagagtcatc    3988
agtacattgg tttgcagaaa tcttttacag gctacatttt ggattttttt ttttttagt    4048 aagtgatcaa atttggtggg aagtaattcg agtgtattcg attgtattgt cgtcctcgtt    4108
atcattgtca acatgttat agacggcagt tggcactggg gctgctaatc tctgggtgta    4168
gtctctgaaa ctgtagctcc agtgaggtgg tgtgaaaggt tagcaaagcc accatctgct    4228
ggtggctcca gccaaggtgc ctcttagcca ctgaattgct atgttatcct ttctcttgta    4288
acaaacccac cccagagata aagcctttaa tcaacccaag aaactcctgg gctaagtatc    4348
tgacagtctc acatctcaac agtgtgaatt aagtgtccat agcatcagct caggaggaca    4408
ctctgggaga gtgctgacaa aaagggtta ttaatactga cctactactt caagggcagt    4468
tctgaggtga ttagagcttt ttttaaaaac caagtatttg gggatcctca gcagaggtat    4528
tcatacagac tcccaaagaa ctatatatgt tcctgagacc atcgtttagt ctacattgct    4588
cttcccagag actgacagat atgaccagtc aaagtgcaag actacctacc cactgccatg    4648
aaaaccattg caggaaacct ttcccttccc tgaatgagat tttttttttc ccttttatg    4708 tggggtaatt atttgtgacc caagtgtaat ttggatgatt tccattaata tcaactcttg    4768
aagcctactt gtactgattg agattgtatt tgttcctaat aaaagtggat ctggttgtac    4828
tgtctgggaa aaaaaa                                                    4844
```

<210> SEQ ID NO 6
<211> LENGTH: 355
<212> TYPE: PRT
<213> ORGANISM: Mus musculus

<400> SEQUENCE: 6

```
Met Pro Ala His Met Leu Gln Glu Ile Ser Ser Tyr Thr Thr Thr
1               5                   10                  15

Thr Thr Ile Thr Ala Pro Pro Ser Gly Asn Glu Arg Glu Lys Val Lys
            20                  25                  30

Thr Val Pro Leu His Leu Glu Glu Asp Ile Arg Pro Glu Met Lys Glu
        35                  40                  45

Asp Ile His Asp Pro Thr Tyr Gln Asp Glu Gly Pro Pro Lys
    50                  55                  60

Leu Glu Tyr Val Trp Arg Asn Ile Ile Leu Met Val Leu Leu His Leu
65                  70                  75                  80

Gly Gly Leu Tyr Gly Ile Ile Leu Val Pro Ser Cys Lys Leu Tyr Thr
                85                  90                  95

Cys Leu Phe Gly Ile Phe Tyr Tyr Met Thr Ser Ala Leu Gly Ile Thr
            100                 105                 110

Ala Gly Ala His Arg Leu Trp Ser His Arg Thr Tyr Lys Ala Arg Leu
        115                 120                 125

Pro Leu Arg Ile Phe Leu Ile Ile Ala Asn Thr Met Ala Phe Gln Asn
    130                 135                 140

Asp Val Tyr Glu Trp Ala Arg Asp His Arg Ala His His Lys Phe Ser
145                 150                 155                 160

Glu Thr His Ala Asp Pro His Asn Ser Arg Arg Gly Phe Phe Phe Ser
                165                 170                 175

His Val Gly Trp Leu Leu Val Arg Lys His Pro Ala Val Lys Glu Lys
            180                 185                 190
```

Gly Gly Lys Leu Asp Met Ser Asp Leu Lys Ala Glu Lys Leu Val Met
        195                 200                 205

Phe Gln Arg Arg Tyr Tyr Lys Pro Gly Leu Leu Leu Met Cys Phe Ile
210                 215                 220

Leu Pro Thr Leu Val Pro Trp Tyr Cys Trp Gly Glu Thr Phe Val Asn
225                 230                 235                 240

Ser Leu Phe Val Ser Thr Phe Leu Arg Tyr Thr Leu Val Leu Asn Ala
                245                 250                 255

Thr Trp Leu Val Asn Ser Ala Ala His Leu Tyr Gly Tyr Arg Pro Tyr
                260                 265                 270

Asp Lys Asn Ile Gln Ser Arg Glu Asn Ile Leu Val Ser Leu Gly Ala
        275                 280                 285

Val Gly Glu Gly Phe His Asn Tyr His His Thr Phe Pro Phe Asp Tyr
290                 295                 300

Ser Ala Ser Glu Tyr Arg Trp His Ile Asn Phe Thr Thr Phe Phe Ile
305                 310                 315                 320

Asp Cys Met Ala Ala Leu Gly Leu Ala Tyr Asp Arg Lys Lys Val Ser
                325                 330                 335

Lys Ala Thr Val Leu Ala Arg Ile Lys Arg Thr Gly Asp Gly Ser His
                340                 345                 350

Lys Ser Ser
        355

<210> SEQ ID NO 7
<211> LENGTH: 20
<212> TYPE: DNA
<213> ORGANISM: Artificial
<220> FEATURE:
<223> OTHER INFORMATION: T3 primer

<400> SEQUENCE: 7
aattaaccct cactaaaggg                                               20

<210> SEQ ID NO 8
<211> LENGTH: 19
<212> TYPE: DNA
<213> ORGANISM: Artificial
<220> FEATURE:
<223> OTHER INFORMATION: T7 primer

<400> SEQUENCE: 8
taatacgact cactatagg                                                19

<210> SEQ ID NO 9
<211> LENGTH: 20
<212> TYPE: DNA
<213> ORGANISM: Artificial
<220> FEATURE:
<223> OTHER INFORMATION: primer sense

<400> SEQUENCE: 9
gttgatgtgc ttcatcctgc                                               20

<210> SEQ ID NO 10
<211> LENGTH: 20
<212> TYPE: DNA
<213> ORGANISM: Artificial
<220> FEATURE:
<223> OTHER INFORMATION: primer antisense

<400> SEQUENCE: 10

```
aggtggtgaa gttgatgtgc                                              20

<210> SEQ ID NO 11
<211> LENGTH: 20
<212> TYPE: DNA
<213> ORGANISM: Artificial
<220> FEATURE:
<223> OTHER INFORMATION: primer sense

<400> SEQUENCE: 11
gatgatgtgc ttcatcctgc                                              20

<210> SEQ ID NO 12
<211> LENGTH: 20
<212> TYPE: DNA
<213> ORGANISM: Artificial
<220> FEATURE:
<223> OTHER INFORMATION: primer antisense

<400> SEQUENCE: 12
tgtggtgaag ttgatgtgcc                                              20

<210> SEQ ID NO 13
<211> LENGTH: 20
<212> TYPE: DNA
<213> ORGANISM: Artificial
<220> FEATURE:
<223> OTHER INFORMATION: primer antisense

<400> SEQUENCE: 13
tggcttcttc ttctctcacg                                              20

<210> SEQ ID NO 14
<211> LENGTH: 20
<212> TYPE: DNA
<213> ORGANISM: Artificial
<220> FEATURE:
<223> OTHER INFORMATION: primer antisense

<400> SEQUENCE: 14
atatccatag agatgcgcgg                                              20

<210> SEQ ID NO 15
<211> LENGTH: 18
<212> TYPE: DNA
<213> ORGANISM: Artificial
<220> FEATURE:
<223> OTHER INFORMATION: GAPDH primer

<400> SEQUENCE: 15
gggctgcttt taactctg                                                18

<210> SEQ ID NO 16
<211> LENGTH: 18
<212> TYPE: DNA
<213> ORGANISM: Artificial
<220> FEATURE:
<223> OTHER INFORMATION: GAPDH primer

<400> SEQUENCE: 16
ccaggaaatg agcttgac                                                18

<210> SEQ ID NO 17
<211> LENGTH: 20
<212> TYPE: DNA
```

```
<213> ORGANISM: Artificial
<220> FEATURE:
<223> OTHER INFORMATION: gapdh primer

<400> SEQUENCE: 17
cttcaccacc atggagaagg                                                     20

<210> SEQ ID NO 18
<211> LENGTH: 20
<212> TYPE: DNA
<213> ORGANISM: Artificial
<220> FEATURE:
<223> OTHER INFORMATION: gapdh primer

<400> SEQUENCE: 18
tgaagtcgca ggagacaacc                                                     20

<210> SEQ ID NO 19
<211> LENGTH: 24
<212> TYPE: DNA
<213> ORGANISM: Artificial
<220> FEATURE:
<223> OTHER INFORMATION: primer sense

<400> SEQUENCE: 19
atgccggccc acatgctcca agag                                                24

<210> SEQ ID NO 20
<211> LENGTH: 27
<212> TYPE: DNA
<213> ORGANISM: Artificial
<220> FEATURE:
<223> OTHER INFORMATION: primer antisense

<400> SEQUENCE: 20
tcagctactc ttgtgactcc cgtctcc                                             27

<210> SEQ ID NO 21
<211> LENGTH: 5108
<212> TYPE: DNA
<213> ORGANISM: Bos taurus
<220> FEATURE:
<221> NAME/KEY: CDS
<222> LOCATION: (145)..(1224)
<223> OTHER INFORMATION:

<400> SEQUENCE: 21
tgcagcggaa ggtcccgagc gcagcgctgc ggatccccac gcaaaagcag gctcaggaac         60
tagtctacac tcagtttgga ctgccccgaa ctccgctccg cagtctcagc cccgagaaag        120
tgatcccagt gtctgagagc ccag atg ccg gcc cac ttg ctg caa gag gag          171
                          Met Pro Ala His Leu Leu Gln Glu Glu
                           1               5 atc tct agc tcc tac aca acc acc acc acc atc aca gca cct cct tcc        219
Ile Ser Ser Ser Tyr Thr Thr Thr Thr Thr Ile Thr Ala Pro Pro Ser
 10              15                  20                  25 agg gtc ctg cag aat gga ggg ggc aaa ttg gag aag act ccc cta tac        267
Arg Val Leu Gln Asn Gly Gly Gly Lys Leu Glu Lys Thr Pro Leu Tyr
                 30                  35                  40 ttg gaa gaa gac atc cgc cct gaa atg aga gat gac atc tat gac cca        315
Leu Glu Glu Asp Ile Arg Pro Glu Met Arg Asp Asp Ile Tyr Asp Pro
             45                  50                  55 act tac cag gat aag gag ggc cca aag ccc aag ctt gag tat gtt tgg        363
Thr Tyr Gln Asp Lys Glu Gly Pro Lys Pro Lys Leu Glu Tyr Val Trp
         60                  65                  70
```

```
aga aac atc atc ctc atg tct ctg tta cac ttg gga gcc cta tat ggg      411
Arg Asn Ile Ile Leu Met Ser Leu Leu His Leu Gly Ala Leu Tyr Gly
     75                  80                  85 atc aca ttg atc ccc acc tgc aag ata tac acc tat atc tgg gtg tta      459
Ile Thr Leu Ile Pro Thr Cys Lys Ile Tyr Thr Tyr Ile Trp Val Leu
 90                  95                 100                 105 ttc tac tat ctg atg ggt gcc ctg ggc atc aca gca ggg gcc cat cgc      507
Phe Tyr Tyr Leu Met Gly Ala Leu Gly Ile Thr Ala Gly Ala His Arg
                    110                 115                 120 ctg tgg agt cac cga acc tac aaa gct cgg ctg cct ctg cgg gtc ttc      555
Leu Trp Ser His Arg Thr Tyr Lys Ala Arg Leu Pro Leu Arg Val Phe
                125                 130                 135 ctg atc att ggc aac acc atg gcg ttc cag aat gac gtt ttt gaa tgg      603
Leu Ile Ile Gly Asn Thr Met Ala Phe Gln Asn Asp Val Phe Glu Trp
            140                 145                 150 tcc cga gat cac cgt gcc cac cac aag ttt tca gaa acg gat gcc gac      651
Ser Arg Asp His Arg Ala His His Lys Phe Ser Glu Thr Asp Ala Asp
        155                 160                 165 ccc cac aat tcc cga cgt ggc ttt ttc ttc tct cac gtg ggt tgg ctg      699
Pro His Asn Ser Arg Arg Gly Phe Phe Phe Ser His Val Gly Trp Leu
170                 175                 180                 185 ctt gtg cgc aaa cac cca gct gtc aaa gaa aag ggt tcc acg cta aat      747
Leu Val Arg Lys His Pro Ala Val Lys Glu Lys Gly Ser Thr Leu Asn
                190                 195                 200 tta tcc gac cta aga gcc gag aag ctg gtg atg ttc cag agg agg tac      795
Leu Ser Asp Leu Arg Ala Glu Lys Leu Val Met Phe Gln Arg Arg Tyr
            205                 210                 215 tac aaa cct ggt gtc ctg ttg ttg tgc ttc atc ctg ccc aca ctc gtg      843
Tyr Lys Pro Gly Val Leu Leu Leu Cys Phe Ile Leu Pro Thr Leu Val
        220                 225                 230 cca tgg tat ctg tgg gat gaa acg ttt caa aac agc ctg ttt ttt gcc      891
Pro Trp Tyr Leu Trp Asp Glu Thr Phe Gln Asn Ser Leu Phe Phe Ala
235                 240                 245 acc tta ttc cgt tat gcc ctt ggg ctc aac gtc acc tgg ctg gtg aat      939
Thr Leu Phe Arg Tyr Ala Leu Gly Leu Asn Val Thr Trp Leu Val Asn
250                 255                 260                 265 agt gct gcc cat atg tat gga tac cgc cct tat gac aag acc atc aac      987
Ser Ala Ala His Met Tyr Gly Tyr Arg Pro Tyr Asp Lys Thr Ile Asn
                270                 275                 280 ccc cga gag aat att ctg gtt tcc ctg gga gct gcg ggt gag ggc ttc     1035
Pro Arg Glu Asn Ile Leu Val Ser Leu Gly Ala Ala Gly Glu Gly Phe
            285                 290                 295 cac aac tac cac cac acc ttt cct tat gac tac tca gcc agt gag tac     1083
His Asn Tyr His His Thr Phe Pro Tyr Asp Tyr Ser Ala Ser Glu Tyr
        300                 305                 310 cgc tgg cac atc aac ttt acc acg ttc ttc att gat tgc atg gct gcc     1131
Arg Trp His Ile Asn Phe Thr Thr Phe Phe Ile Asp Cys Met Ala Ala
315                 320                 325 atc ggt ctg gct tat gac cgg aag aaa gta tcc aag gct gcc atc ttg     1179
Ile Gly Leu Ala Tyr Asp Arg Lys Lys Val Ser Lys Ala Ala Ile Leu
330                 335                 340                 345 gcc agg ata aaa aga act gga gag gaa agc tac aag agt ggc tga         1224
Ala Arg Ile Lys Arg Thr Gly Glu Glu Ser Tyr Lys Ser Gly
                350                 355 atttgtggtc ccttgggttc cttttccaaa agccatctgg gcagaggttt aatgttctgt     1284
ttattaacta ctgaataatg ctaccaggat gctaaagatg acgttaaccc attacagtac     1344
agtattcttt aaaatttttct ttttaaattg aaagccaaca actctgcctt tatgatgcta    1404
```

```
agctcatgtt cttatttctt ctcctatctt ctttctcttc tgttcccatt atccttccct    1464
ttgttttgtc cctgtcacct tcctttctcc ttctcctcat tgccccccag gcaagcaggt    1524
ggtcagtcat tggtgggttt ccagcttcca aagcctagac aaccctgctg tagtctcaaa    1584
ctagtggtct ttgccccggc tgaccctttc cttgagctgt ctgagcttta aggtggatgg    1644
ctcaagctag agatatgaca gaatcttctg ggaagggcct tgatgatctt cagcccagac    1704
ttttgctaaa tgaaatggaa aaataacttt attttggcac caaactgaaa aaacaggtca    1764
attgtcaggg gagagagtca gcatgcatgg tgtgattgat aaataggatg agttgaagtg    1824
ggaaacaagg caggaagctc ctgctgtgat cagacacccc tgtctgccca tcacccagta    1884
tgctcccttt ctctcctgac tctgggaaat atctgtggag cagggcagtc ctaaaactca    1944
aaagcaaatc tcaatgtcct gatatacttt aggcttagga taaagaagaa gcatttagtt    2004
tgtggtaaaa gtggtctctg ctgcagacga attgttttct ttctttcaca acaggaagat    2064
ttcttattct agataacaag aaatcttgag gttggttatt tccagaattg ctgattccag    2124
cagctcagga aattgtcaaa attctttcat cttttctactc tgccatcttg gggatattgg   2184
tcagctcccc tcatagtaag aagatggcta cagcattttg agacttcaaa aagagataca    2244
ttggtggtat ggtggtgagc atagctgcct cccaaaaaag aaagaatttt aggagccaga    2304
gttgggtcaa acataaagct atatatacat gggtactttg gttggaatat taaagtaatt    2364
ctcttagagt atttccctct gaaagagagg gggcttgaag aagaggaaga attagccagg    2424
ttgcctcctt tcctctcgct gctggacagg agatggagag gttgaggggc agggtctgta    2484
ggcagttcct aagagatagg gttacaaaag aaaggctctg agatcacatt gctgggggat    2544
tcagaaggtt actgagtaag ttgttgggtg tcctgatata aagctggtt atacaaacaa     2604 gttagatgtt gggttcattt cattaattcc actttctcct tggattgaga aagcattaga    2664
aggtttctcc ccacggtgtt gaacccttc actcattcct tctattaccct tctagcggaa   2724 aatacaggac tggctggggg atggggtagg aatctctcaa ctaccctatc aattcttggc    2784
tctgccatct ttgtccactt tctcctgctg gttttatctc cttgacgttt ccttctttt    2844 ctggacaggc aagcctcttc tgtgtgtatt cagaggcagt gatggctact gcggtccaag    2904
tcgttccctc tcttactgac agaatggtca gggtcactga accactgttt ctctttacaa    2964
agttgagcaa gctgccactt tcacttggcc tccagagtct ccatctatat ccttgtgctc    3024
cttaccacac tgatgactcc agacaaggct ggcaaagcct gctagaaaca tcctgggcac    3084
aggcattcgc actcatgagg cacggccaag ccgaatgctc atgttgtgcc agagccagcc    3144
atggagcaaa agaggatttg ttttagtct cctctgtctg ggtcagaacc agagagcatg    3204
ctggatgccc ccggcttact ggataagctg cctaccctga gtcagtgctc ccagcggaca    3264
gtgcgaggct tgcagaagca gggggtgcct agccttcact gggaagcaca agaagcaaag    3324
gcaggttcca aagtgcctca ctcagaaggt ggccccagcc ccctggaggg agccagggtg    3384
taccgcaaga ccttgactga ggcttaggat gtgagatgcc atgaactttg ctgaacagtg    3444
tctctgttca gcaaactaac cagcattccc cacaacacag tctagggcag acgatagtat    3504
agaggagtgt tggaagaacc ttgggtccct ttgtccctgt aacctcagtt gtctaggcag    3564
aaacctggct ttattctatt taaggttga aaatatacaa taccaaatgc tctgccactg     3624
ttgagctcca aggatggaaa ggaggagaac atttcttcct gtattaattg gatagatgga    3684
ggctacagag cttaggctaa actaaaggca tccttgtctt ttgagttgtt cctctcagta    3744
ggaaaaaaaa aaaatctaat ggaagatcac tgtagattag atcctctgac caagcaccta    3804
```

```
ccgcttggaa atgcctgtgg ggtagtttta attccacagg tcatcagatg catgctttac   3864
aactgatgat caaaaccaac ttatctttct attctaattg tgttccgtgg atctgatcta   3924
taccatgacc ctacacaagg ctggatggtg tccttgggcc cagggtactt gtacttgtgt   3984 aggtggggt  tgtctactga gtaaggaata ctgttttta  ggttctaaag ctaaattcaa   4044
atgatgcatt aatgacccaa aaactcagat ctgatggtgt ctgaatttct aacagtcctt   4104
gctttgtggg tatgctgaca acttatctgg atgccttaca tcttttctaa acagtgttgc   4164
ctctgaacgt gctctgctcc ctccctgctc cctctttgga gccccttgc  accccagagc   4224 ctgcagaagt ggctggtata aaggggcc   tggctagaga atgatcagtg tagctgtttg   4284
caggattcct ttctgggctt cattttggaa actttgctta gggctatttt tcttaattgc   4344
ccacatttga tggagggtag aaggaatttt gaatgtattt gatttattat tattatttt    4404 tttttttag  attaaaggat ggttgtagca tttaaaatgg aaatttttcc tcctggttag   4464
ctagtatcct gagtgtattc tctgtaagtg tagctcaaat gggtcatcat gaaaagttca   4524
agaaagctcg atgtcaaagt tatatgggtg gttaaggcca gggcctgtcc taccactgtg   4584
ccactgactt gctatgtgac cctgggcaag tcatttaact ataatgtgcc tcagtttcc    4644 ttctgttaaa atgggataat aatactgacc tacctcaaag ggcagttttg aggcatgact   4704
aatgcttttt ataaagcatc ttggaattct cttaagttct gagtattttt atagtagcag   4764
tatccaccat gaagtgtgtc caccacgagc cacgtgtcct ggatgccgtc aggaatctat   4824
atggttctct ctgagagatg gaataaatgc atcagataaa gggtggataa ctagccggac   4884
aaaatctgag aatgcataaa ctcattgcca tggaaacata cacaggatac cttttcctta   4944
attgggtggg attttccct  ttttatgtgg gatagtagtt atttgtgacc taagaataat   5004 tttgaataa  tttctattaa tatcaactcc aaagctagtt gtactgatct gagattgtgt   5064
ttgttcataa taaaagtgaa tctgattgcc ctgaaaaaaa aaaa                    5108
```

<210> SEQ ID NO 22
<211> LENGTH: 359
<212> TYPE: PRT
<213> ORGANISM: Bos taurus

<400> SEQUENCE: 22

```
Met Pro Ala His Leu Leu Gln Glu Glu Ile Ser Ser Tyr Thr Thr
1               5                   10                  15

Thr Thr Thr Ile Thr Ala Pro Pro Ser Arg Val Leu Gln Asn Gly Gly
            20                  25                  30

Gly Lys Leu Glu Lys Thr Pro Leu Tyr Leu Glu Glu Asp Ile Arg Pro
        35                  40                  45

Glu Met Arg Asp Asp Ile Tyr Asp Pro Thr Tyr Gln Asp Lys Glu Gly
    50                  55                  60

Pro Lys Pro Lys Leu Glu Tyr Val Trp Arg Asn Ile Ile Leu Met Ser
65                  70                  75                  80

Leu Leu His Leu Gly Ala Leu Tyr Gly Ile Thr Leu Ile Pro Thr Cys
                85                  90                  95

Lys Ile Tyr Thr Tyr Ile Trp Val Leu Phe Tyr Tyr Leu Met Gly Ala
            100                 105                 110

Leu Gly Ile Thr Ala Gly Ala His Arg Leu Trp Ser His Arg Thr Tyr
        115                 120                 125

Lys Ala Arg Leu Pro Leu Arg Val Phe Leu Ile Ile Gly Asn Thr Met
    130                 135                 140
```

```
Ala Phe Gln Asn Asp Val Phe Glu Trp Ser Arg Asp His Arg Ala His
145                 150                 155                 160

His Lys Phe Ser Glu Thr Asp Ala Asp Pro His Asn Ser Arg Arg Gly
                165                 170                 175

Phe Phe Phe Ser His Val Gly Trp Leu Leu Val Arg Lys His Pro Ala
            180                 185                 190

Val Lys Glu Lys Gly Ser Thr Leu Asn Leu Ser Asp Leu Arg Ala Glu
            195                 200                 205

Lys Leu Val Met Phe Gln Arg Arg Tyr Tyr Lys Pro Gly Val Leu Leu
210                 215                 220

Leu Cys Phe Ile Leu Pro Thr Leu Val Pro Trp Tyr Leu Trp Asp Glu
225                 230                 235                 240

Thr Phe Gln Asn Ser Leu Phe Phe Ala Thr Leu Phe Arg Tyr Ala Leu
                245                 250                 255

Gly Leu Asn Val Thr Trp Leu Val Asn Ser Ala Ala His Met Tyr Gly
            260                 265                 270

Tyr Arg Pro Tyr Asp Lys Thr Ile Asn Pro Arg Glu Asn Ile Leu Val
            275                 280                 285

Ser Leu Gly Ala Ala Gly Glu Gly Phe His Asn Tyr His His Thr Phe
290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Ala Ile Gly Leu Ala Tyr Asp Arg
                325                 330                 335

Lys Lys Val Ser Lys Ala Ala Ile Leu Ala Arg Ile Lys Arg Thr Gly
            340                 345                 350

Glu Glu Ser Tyr Lys Ser Gly
            355
```

<210> SEQ ID NO 23
<211> LENGTH: 1080
<212> TYPE: DNA
<213> ORGANISM: Equus caballus
<220> FEATURE:
<221> NAME/KEY: CDS
<222> LOCATION: (1)..(1080)
<223> OTHER INFORMATION:

<400> SEQUENCE: 23

```
atg ccg gcc cat ttg ctg caa gag gag atc tct agc tcc tac act acc       48
Met Pro Ala His Leu Leu Gln Glu Glu Ile Ser Ser Ser Tyr Thr Thr
1               5                   10                  15 acc acc acc atc aca gcg cct ccc tcc agg gtc ctg cag aat gga gga       96
Thr Thr Thr Ile Thr Ala Pro Pro Ser Arg Val Leu Gln Asn Gly Gly
            20                  25                  30 ggc aag ttg gag aag act tcc cca tac ttg gaa gaa gac atc cgc cct      144
Gly Lys Leu Glu Lys Thr Ser Pro Tyr Leu Glu Glu Asp Ile Arg Pro
        35                  40                  45 gaa atg aaa gaa gac ctc tat gac ccg agc tac cgg gat aag gag ggc      192
Glu Met Lys Glu Asp Leu Tyr Asp Pro Ser Tyr Arg Asp Lys Glu Gly
    50                  55                  60 cca aag ccc aag ttt cag tat gtt tgg aga aac atc atc ctt atg tct      240
Pro Lys Pro Lys Phe Gln Tyr Val Trp Arg Asn Ile Ile Leu Met Ser
65                  70                  75                  80 ctg cta cac gtg gga gcc ctg tat ggg atc cta ctg ttc ccc agc tgc      288
Leu Leu His Val Gly Ala Leu Tyr Gly Ile Leu Leu Phe Pro Ser Cys
                85                  90                  95
```

| | | |
|---|---|---|
| aag atc tac acc tac ctc tgg gtg gct ttc tac tat ttc acc agt gcc<br>Lys Ile Tyr Thr Tyr Leu Trp Val Ala Phe Tyr Tyr Phe Thr Ser Ala<br>100 105 110 | | 336 |
| ctt ggc gta acg gca gga gcg cat cgc ctg tgg agc cac cgg act tac<br>Leu Gly Val Thr Ala Gly Ala His Arg Leu Trp Ser His Arg Thr Tyr<br>115 120 125 | | 384 |
| aaa gct cgg ctg ccc ctg cgt ctc ttc ctg atc att gcc aac acg atg<br>Lys Ala Arg Leu Pro Leu Arg Leu Phe Leu Ile Ile Ala Asn Thr Met<br>130 135 140 | | 432 |
| gcc ttc cag aat gac att ttt gaa tgg gcc cga gat cac cgt gtc cac<br>Ala Phe Gln Asn Asp Ile Phe Glu Trp Ala Arg Asp His Arg Val His<br>145 150 155 160 | | 480 |
| cac aag ttt tca gaa aca gat gct gat ccc cac aat gcc cga cgt ggc<br>His Lys Phe Ser Glu Thr Asp Ala Asp Pro His Asn Ala Arg Arg Gly<br>165 170 175 | | 528 |
| ttt ttc ttc tct cac gtg ggt tgg ctg ctt gtg cgc aaa cac cca gca<br>Phe Phe Phe Ser His Val Gly Trp Leu Leu Val Arg Lys His Pro Ala<br>180 185 190 | | 576 |
| gtc aaa gag aaa ggt gct ttg cta gag tta tct gac cta aaa gcc gag<br>Val Lys Glu Lys Gly Ala Leu Leu Glu Leu Ser Asp Leu Lys Ala Glu<br>195 200 205 | | 624 |
| aag ctg gtg atg ttc cag agg agg tac tac aaa ccc ggt gtc gtg ttg<br>Lys Leu Val Met Phe Gln Arg Arg Tyr Tyr Lys Pro Gly Val Val Leu<br>210 215 220 | | 672 |
| ctg tgc ttc atc ctg ccc aca ctt gtg ccc tgg tat ttc tgg ggt gaa<br>Leu Cys Phe Ile Leu Pro Thr Leu Val Pro Trp Tyr Phe Trp Gly Glu<br>225 230 235 240 | | 720 |
| act ttt cca cac agc tta ttt gtc gcc act ttg ttg cgt tac gct ctt<br>Thr Phe Pro His Ser Leu Phe Val Ala Thr Leu Leu Arg Tyr Ala Leu<br>245 250 255 | | 768 |
| gtg ctc aat gtc act tgg ctg gtg aac agt gct gcc cac ctc tac gga<br>Val Leu Asn Val Thr Trp Leu Val Asn Ser Ala Ala His Leu Tyr Gly<br>260 265 270 | | 816 |
| tat cgt cct tac gac aag acc att aac ccc cga gag aat atc ctg gtt<br>Tyr Arg Pro Tyr Asp Lys Thr Ile Asn Pro Arg Glu Asn Ile Leu Val<br>275 280 285 | | 864 |
| tca ctg gga gct gtg ggt gag ggc ttc cac aac tac cac cac tcc ttt<br>Ser Leu Gly Ala Val Gly Glu Gly Phe His Asn Tyr His His Ser Phe<br>290 295 300 | | 912 |
| ccc tat gac tac tct gcc agt gag tac cgc tgg cac atc aac ttt acc<br>Pro Tyr Asp Tyr Ser Ala Ser Glu Tyr Arg Trp His Ile Asn Phe Thr<br>305 310 315 320 | | 960 |
| aca ttc ttc atc gat tgc atg gct gtc ctc ggt ttg gct tat gac cgg<br>Thr Phe Phe Ile Asp Cys Met Ala Val Leu Gly Leu Ala Tyr Asp Arg<br>325 330 335 | | 1008 |
| aag aaa gta tcc aag gct gcc atc ttg gcc aag att aaa aga act gga<br>Lys Lys Val Ser Lys Ala Ala Ile Leu Ala Lys Ile Lys Arg Thr Gly<br>340 345 350 | | 1056 |
| gat gaa acc tac aag agt ggc tga<br>Asp Glu Thr Tyr Lys Ser Gly<br>355 | | 1080 |

<210> SEQ ID NO 24
<211> LENGTH: 359
<212> TYPE: PRT
<213> ORGANISM: Equus caballus

<400> SEQUENCE: 24

Met Pro Ala His Leu Leu Gln Glu Glu Ile Ser Ser Tyr Thr Thr
1               5                   10                  15

Thr Thr Thr Ile Thr Ala Pro Pro Ser Arg Val Leu Gln Asn Gly Gly
            20                  25                  30

Gly Lys Leu Glu Lys Thr Ser Pro Tyr Leu Glu Glu Asp Ile Arg Pro
        35                  40                  45

Glu Met Lys Glu Asp Leu Tyr Asp Pro Ser Tyr Arg Asp Lys Glu Gly
50                  55                  60

Pro Lys Pro Lys Phe Gln Tyr Val Trp Arg Asn Ile Ile Leu Met Ser
65                  70                  75                  80

Leu Leu His Val Gly Ala Leu Tyr Gly Ile Leu Leu Phe Pro Ser Cys
                85                  90                  95

Lys Ile Tyr Thr Tyr Leu Trp Val Ala Phe Tyr Phe Thr Ser Ala
            100                 105                 110

Leu Gly Val Thr Ala Gly Ala His Arg Leu Trp Ser His Arg Thr Tyr
            115                 120                 125

Lys Ala Arg Leu Pro Leu Arg Leu Phe Leu Ile Ile Ala Asn Thr Met
130                 135                 140

Ala Phe Gln Asn Asp Ile Phe Glu Trp Ala Arg Asp His Arg Val His
145                 150                 155                 160

His Lys Phe Ser Glu Thr Asp Ala Asp Pro His Asn Ala Arg Arg Gly
                165                 170                 175

Phe Phe Phe Ser His Val Gly Trp Leu Leu Val Arg Lys His Pro Ala
            180                 185                 190

Val Lys Glu Lys Gly Ala Leu Leu Glu Leu Ser Asp Leu Lys Ala Glu
            195                 200                 205

Lys Leu Val Met Phe Gln Arg Arg Tyr Tyr Lys Pro Gly Val Val Leu
210                 215                 220

Leu Cys Phe Ile Leu Pro Thr Leu Val Pro Trp Tyr Phe Trp Gly Glu
225                 230                 235                 240

Thr Phe Pro His Ser Leu Phe Val Ala Thr Leu Leu Arg Tyr Ala Leu
                245                 250                 255

Val Leu Asn Val Thr Trp Leu Val Asn Ser Ala Ala His Leu Tyr Gly
            260                 265                 270

Tyr Arg Pro Tyr Asp Lys Thr Ile Asn Pro Arg Glu Asn Ile Leu Val
            275                 280                 285

Ser Leu Gly Ala Val Gly Glu Gly Phe His Asn Tyr His His Ser Phe
290                 295                 300

Pro Tyr Asp Tyr Ser Ala Ser Glu Tyr Arg Trp His Ile Asn Phe Thr
305                 310                 315                 320

Thr Phe Phe Ile Asp Cys Met Ala Val Leu Gly Leu Ala Tyr Asp Arg
                325                 330                 335

Lys Lys Val Ser Lys Ala Ala Ile Leu Ala Lys Ile Lys Arg Thr Gly
            340                 345                 350

Asp Glu Thr Tyr Lys Ser Gly
        355

<210> SEQ ID NO 25
<211> LENGTH: 32
<212> TYPE: DNA
<213> ORGANISM: Artificial
<220> FEATURE:
<223> OTHER INFORMATION: primer sense

<400> SEQUENCE: 25
cccggaattc atgccggccc acttgctgca gg                             32

```
<210> SEQ ID NO 26
<211> LENGTH: 44
<212> TYPE: DNA
<213> ORGANISM: Artificial
<220> FEATURE:
<223> OTHER INFORMATION: primer antisense

<400> SEQUENCE: 26
ccgccgctcg agtcagccac tcttgtagtt tccatctccg gttc                          44

<210> SEQ ID NO 27
<211> LENGTH: 491
<212> TYPE: PRT
<213> ORGANISM: Megathura crenulata

<400> SEQUENCE: 27
```

| | | | | | | | | | | | | | | |
|---|---|---|---|---|---|---|---|---|---|---|---|---|---|---|
| Ile | Leu | Val | Arg | Lys | Asn | Ile | His | Ser | Leu | Ser | His | His | Glu | Ala | Glu |
| 1 | | | | 5 | | | | | 10 | | | | | 15 | |
| Glu | Leu | Arg | Asp | Ala | Leu | Tyr | Lys | Leu | Gln | Asn | Asp | Glu | Ser | His | Gly |
| | | | 20 | | | | | 25 | | | | | 30 | | |
| Gly | Tyr | Glu | His | Ile | Ala | Gly | Phe | His | Gly | Tyr | Pro | Asn | Leu | Cys | Pro |
| | | 35 | | | | | 40 | | | | | 45 | | | |
| Glu | Lys | Gly | Asp | Glu | Lys | Tyr | Pro | Cys | Cys | Val | His | Gly | Met | Ser | Ile |
| | 50 | | | | | 55 | | | | | 60 | | | | |
| Phe | Pro | His | Trp | His | Arg | Leu | His | Thr | Ile | Gln | Phe | Glu | Arg | Ala | Leu |
| 65 | | | | | 70 | | | | | 75 | | | | | 80 |
| Lys | Lys | His | Gly | Ser | His | Leu | Gly | Ile | Pro | Tyr | Trp | Asp | Trp | Thr | Gln |
| | | | | 85 | | | | | 90 | | | | | 95 | |
| Thr | Ile | Ser | Ser | Leu | Pro | Thr | Phe | Phe | Ala | Asp | Ser | Gly | Asn | Asn | Asn |
| | | | 100 | | | | | 105 | | | | | 110 | | |
| Pro | Phe | Phe | Lys | Tyr | His | Ile | Arg | Ser | Ile | Asn | Gln | Asp | Thr | Val | Arg |
| | | 115 | | | | | 120 | | | | | 125 | | | |
| Asp | Val | Asn | Glu | Ala | Ile | Phe | Gln | Gln | Thr | Lys | Phe | Gly | Glu | Phe | Ser |
| | 130 | | | | | 135 | | | | | 140 | | | | |
| Ser | Ile | Phe | Tyr | Leu | Ala | Leu | Gln | Ala | Leu | Glu | Glu | Asp | Asn | Tyr | Cys |
| 145 | | | | | 150 | | | | | 155 | | | | | 160 |
| Asp | Phe | Glu | Val | Gln | Tyr | Glu | Ile | Leu | His | Asn | Glu | Val | His | Ala | Leu |
| | | | | 165 | | | | | 170 | | | | | 175 | |
| Ile | Gly | Gly | Ala | Glu | Lys | Tyr | Ser | Met | Ser | Thr | Leu | Glu | Tyr | Ser | Ala |
| | | | 180 | | | | | 185 | | | | | 190 | | |
| Phe | Asp | Pro | Tyr | Phe | Met | Ile | His | Ala | Ser | Leu | Asp | Lys | Ile | Trp |
| | | 195 | | | | | 200 | | | | | 205 | | | |
| Ile | Ile | Trp | Gln | Glu | Leu | Gln | Lys | Arg | Arg | Val | Lys | Pro | Ala | His | Ala |
| | 210 | | | | | 215 | | | | | 220 | | | | |
| Gly | Ser | Cys | Ala | Gly | Asp | Ile | Met | His | Val | Pro | Leu | His | Pro | Phe | Asn |
| 225 | | | | | 230 | | | | | 235 | | | | | 240 |
| Tyr | Glu | Ser | Val | Asn | Asn | Asp | Asp | Phe | Thr | Arg | Glu | Asn | Ser | Leu | Pro |
| | | | | 245 | | | | | 250 | | | | | 255 | |
| Asn | Ala | Val | Val | Asp | Ser | His | Arg | Phe | Asn | Tyr | Lys | Tyr | Asp | Asn | Leu |
| | | | 260 | | | | | 265 | | | | | 270 | | |
| Asn | Leu | His | Gly | His | Asn | Ile | Glu | Glu | Leu | Glu | Glu | Val | Leu | Arg | Ser |
| | | 275 | | | | | 280 | | | | | 285 | | | |
| Leu | Arg | Leu | Lys | Ser | Arg | Val | Phe | Ala | Gly | Phe | Val | Leu | Ser | Gly | Ile |
| | 290 | | | | | 295 | | | | | 300 | | | | |
| Arg | Thr | Thr | Ala | Val | Val | Lys | Val | Tyr | Ile | Lys | Ser | Gly | Thr | Asp | Ser |
| 305 | | | | | 310 | | | | | 315 | | | | | 320 |

-continued

```
Asp Asp Glu Tyr Ala Gly Ser Phe Val Ile Leu Gly Gly Ala Lys Glu
            325                 330                 335

Met Pro Trp Ala Tyr Glu Arg Leu Tyr Arg Phe Asp Ile Thr Glu Thr
            340                 345                 350

Val His Asn Leu Asn Leu Thr Asp Asp His Val Lys Phe Arg Phe Asp
            355                 360                 365

Leu Lys Lys Tyr Asp His Thr Glu Leu Asp Ala Ser Val Leu Pro Ala
        370                 375                 380

Pro Ile Ile Val Arg Arg Pro Asn Asn Ala Val Phe Asp Ile Ile Glu
385                 390                 395                 400

Ile Pro Ile Gly Lys Asp Val Asn Leu Pro Pro Lys Val Val Val Lys
                405                 410                 415

Arg Gly Thr Lys Ile Met Phe Met Ser Val Asp Glu Ala Val Thr Thr
                420                 425                 430

Pro Met Leu Asn Leu Gly Ser Tyr Thr Ala Met Phe Lys Cys Lys Val
            435                 440                 445

Pro Pro Phe Ser Phe His Ala Phe Glu Leu Gly Lys Met Tyr Ser Val
        450                 455                 460

Glu Ser Gly Asp Tyr Phe Met Thr Ala Ser Thr Thr Glu Leu Cys Asn
465                 470                 475                 480

Asp Asn Asn Leu Arg Ile His Val His Val Asp
                485                 490
```